United States Patent [19]
Sand et al.

[11] Patent Number: 6,059,790
[45] Date of Patent: May 9, 2000

[54] APPARATUS AND METHOD FOR SPINAL STABILIZATION

[75] Inventors: Paul M. Sand, Roseville; Douglas W. Kohrs; Richard A. Erickson, both of Edina, all of Minn.

[73] Assignee: Sulzer Spine-Tech Inc., Minneapolis, Minn.

[21] Appl. No.: 09/116,747

[22] Filed: Jul. 16, 1998

Related U.S. Application Data

[63] Continuation-in-part of application No. 08/921,001, Aug. 29, 1997.

[51] Int. Cl.[7] .................................................. A61B 17/58
[52] U.S. Cl. ................................. 606/99; 606/61; 606/96
[58] Field of Search ................................ 606/61, 96, 99, 606/104

[56] References Cited

U.S. PATENT DOCUMENTS

| | | |
|---|---|---|
| Re. 36,020 | 12/1998 | Moore et al. ............................ 606/96 |
| D. 397,436 | 8/1998 | Michelson . |
| 5,026,373 | 6/1991 | Ray et al. . |
| 5,055,104 | 10/1991 | Ray . |
| 5,484,437 | 1/1996 | Michelson . |
| 5,489,307 | 2/1996 | Kushlich et al. . |
| 5,505,732 | 4/1996 | Michelson . |
| 5,700,291 | 12/1997 | Kuslich et al. . |
| 5,720,748 | 2/1998 | Kushlich et al. . |
| 5,741,253 | 4/1998 | Michelson . |
| 5,797,909 | 8/1998 | Michelson . |

FOREIGN PATENT DOCUMENTS

| | | |
|---|---|---|
| 0 796 593 A2 | 9/1997 | European Pat. Off. . |
| WO 98/17208 | 4/1998 | WIPO . |

OTHER PUBLICATIONS

Sofamor Danek Brochure: "Surgical Technique Using Bone Dowel Instrumentation".
Sulzer Spine–Tech Brochure: Anterior, 4021 Tooth Tube Surgical Technique, BAK™ Interbody Fusion System.
Declaration of Paul M. Sand.

*Primary Examiner*—Gary Jackson
*Assistant Examiner*—Julian W. Woo
*Attorney, Agent, or Firm*—Merchant & Gould P.C.

[57] ABSTRACT

The disclosure provides a surgical method and apparatus for implanting a spinal fusion implant into an intervertebral disc space. In one embodiment, the invention includes an alignment guide having a distal end sized to be inserted into the disc space with the guide extending along a longitudinal axis from a distal end to a proximal end and a multi-lumen drill tube that can be passed over the alignment guide. Other tools and methods of use are disclosed.

20 Claims, 24 Drawing Sheets

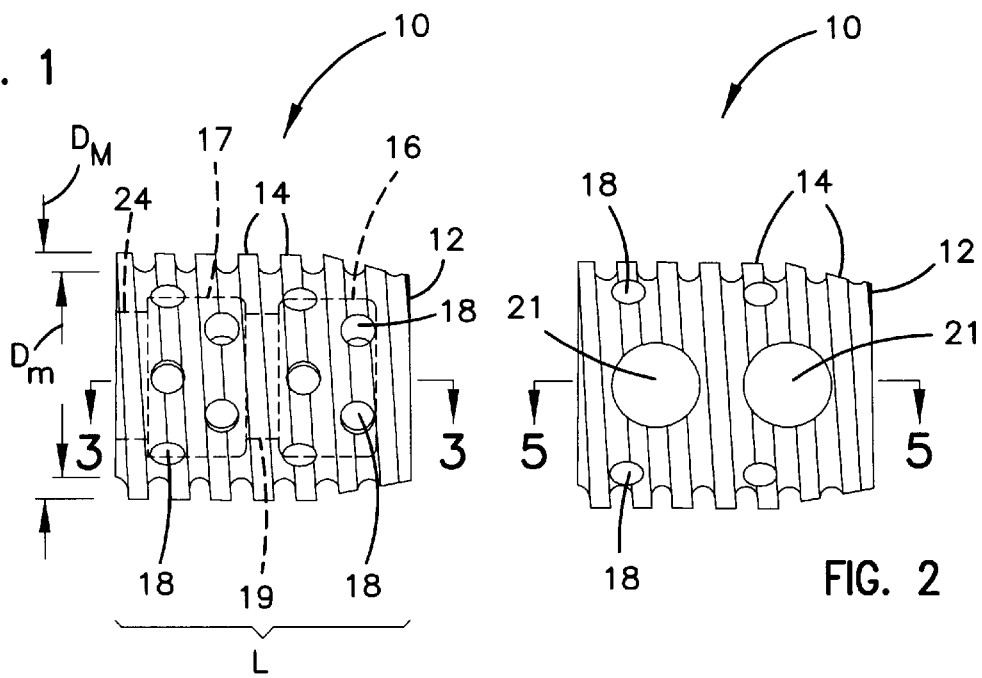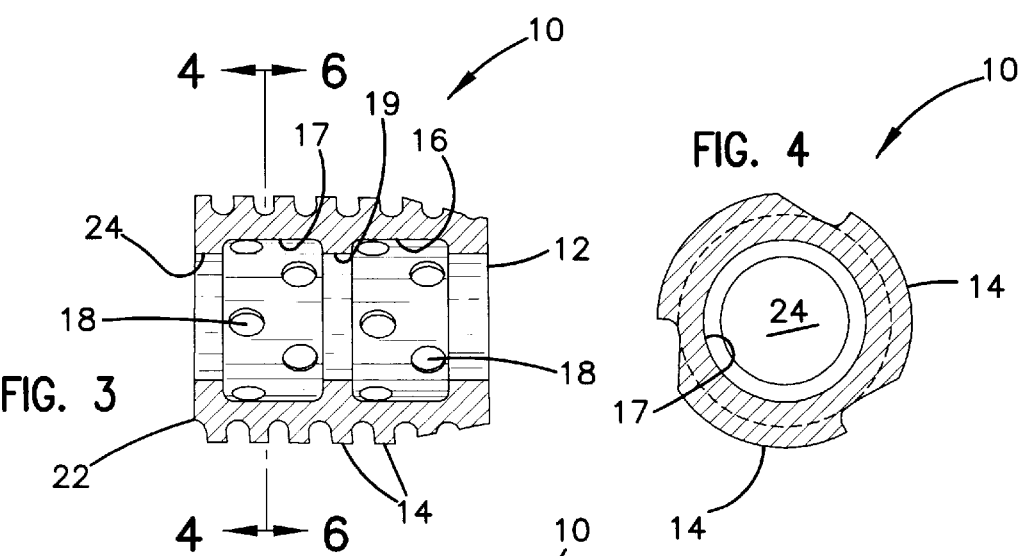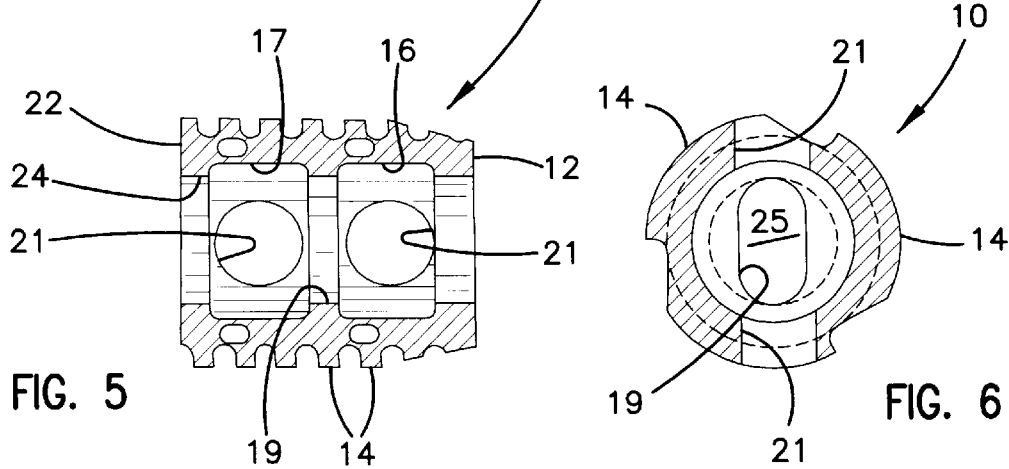

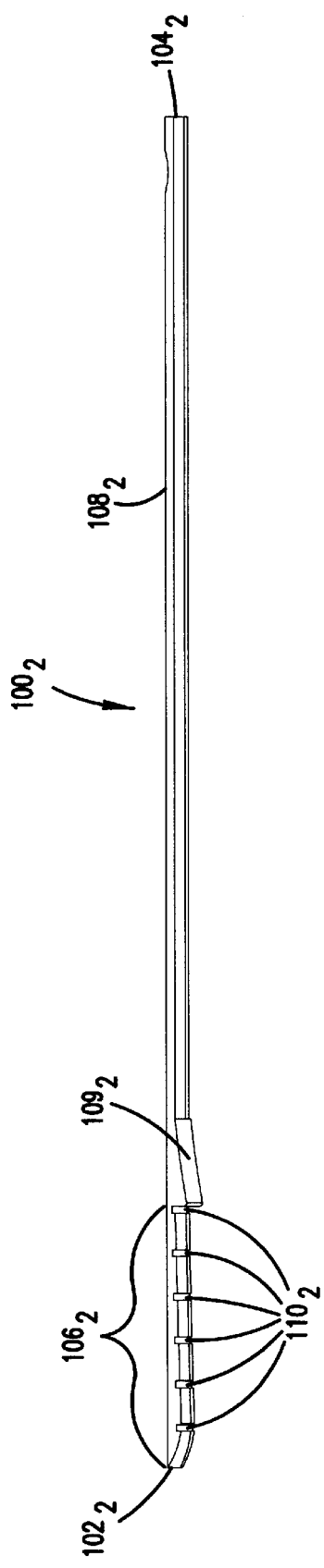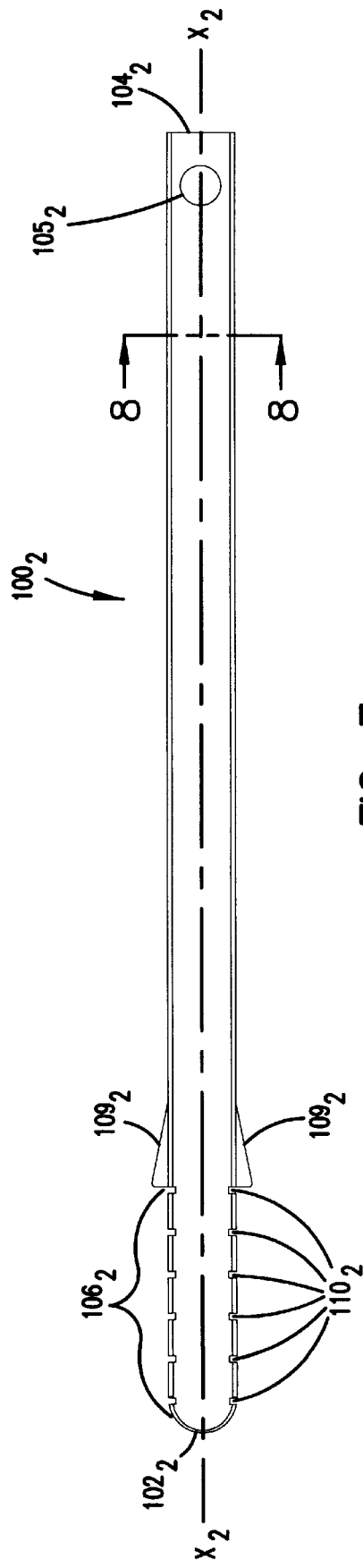

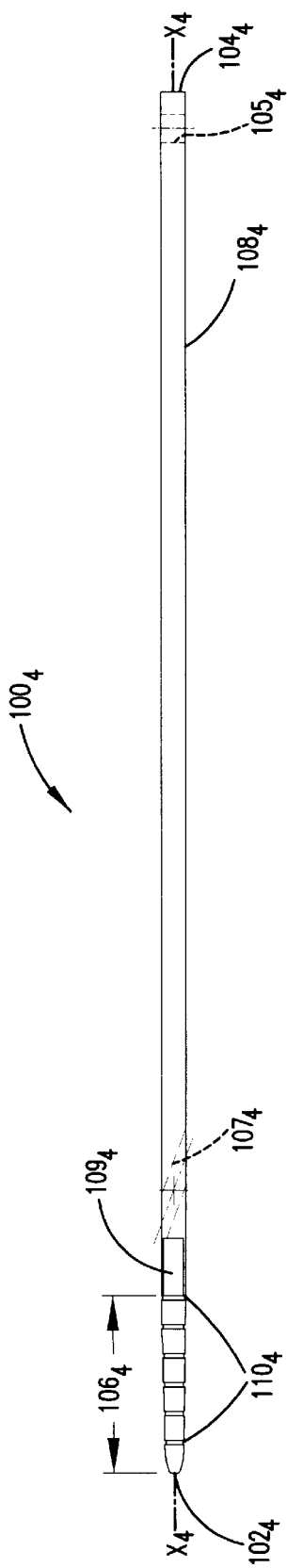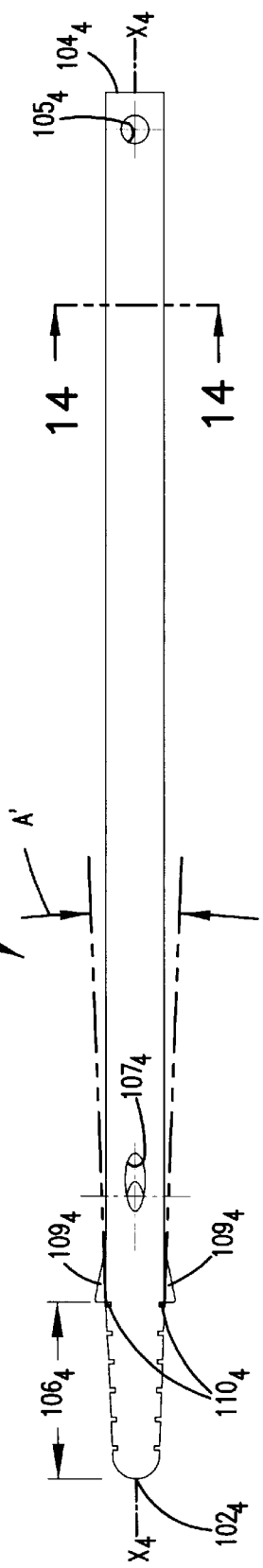
FIG. 15
FIG. 13

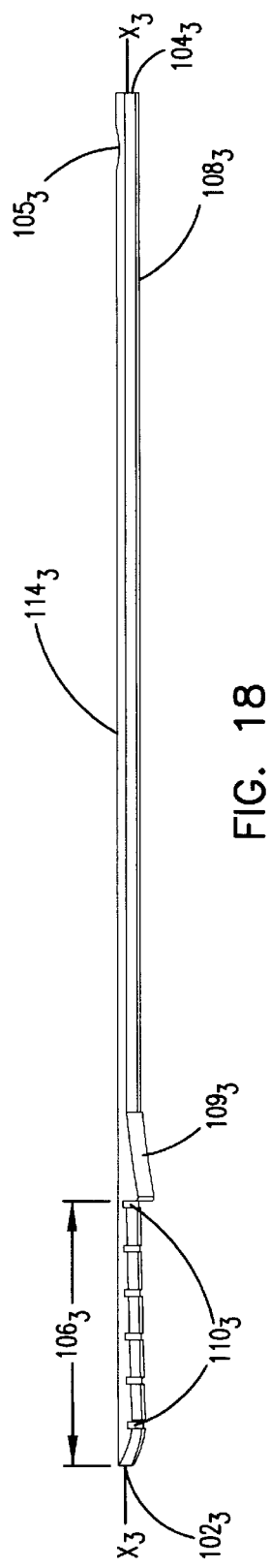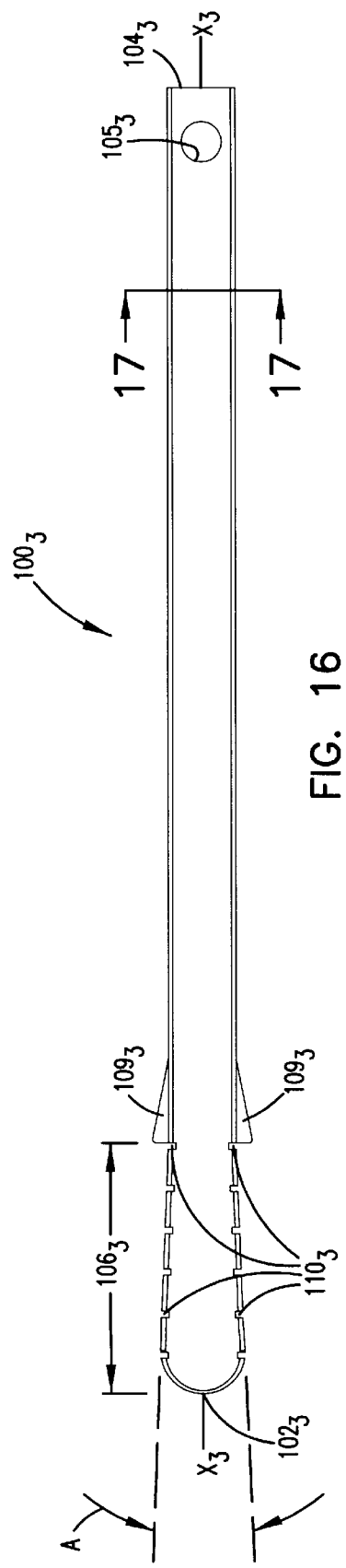

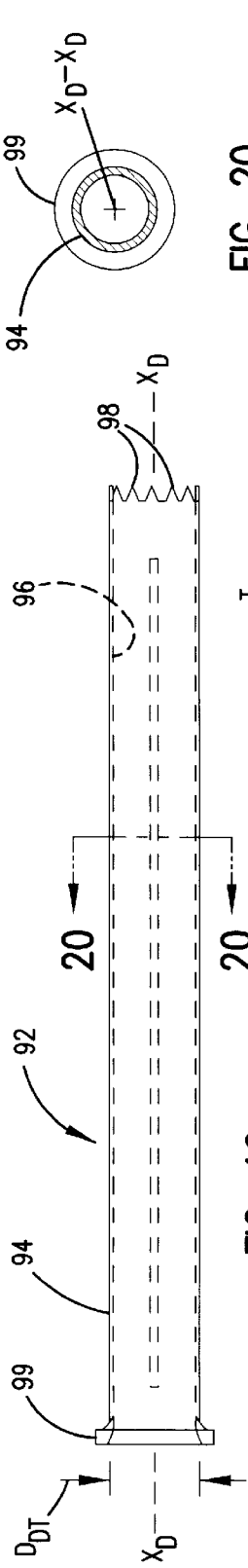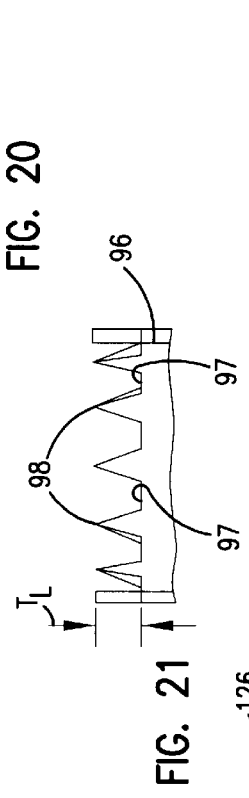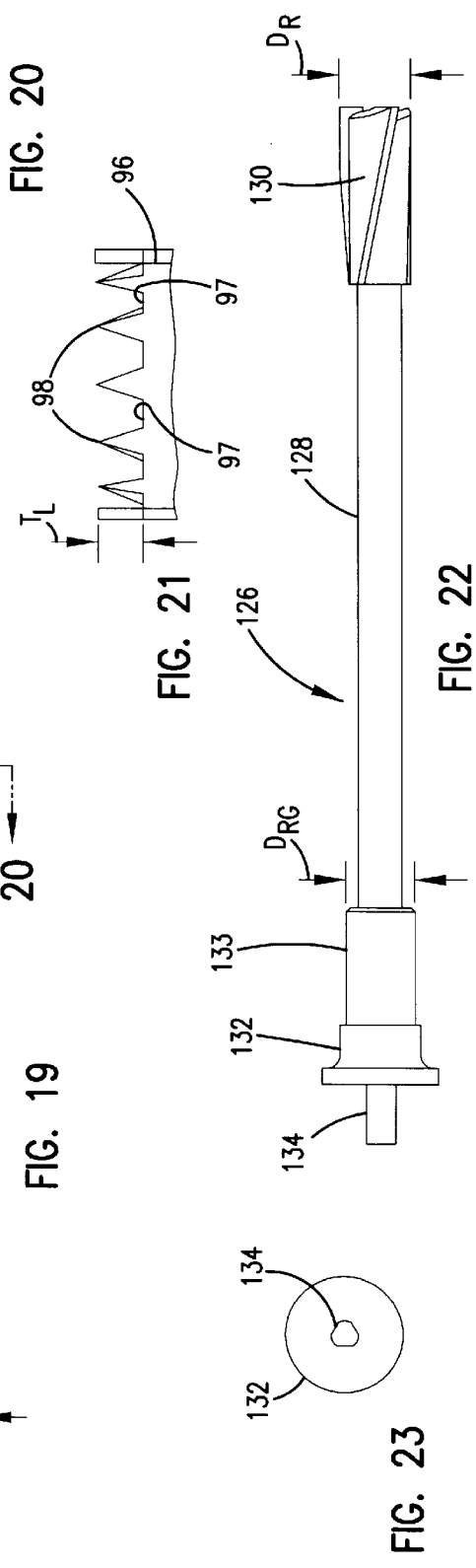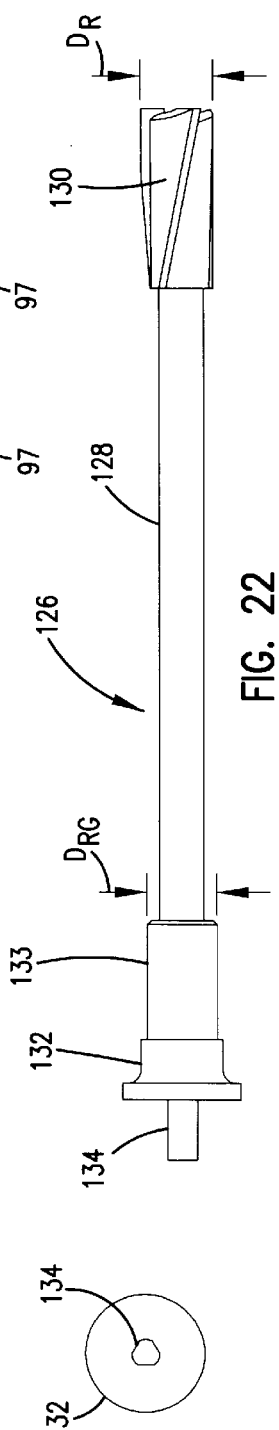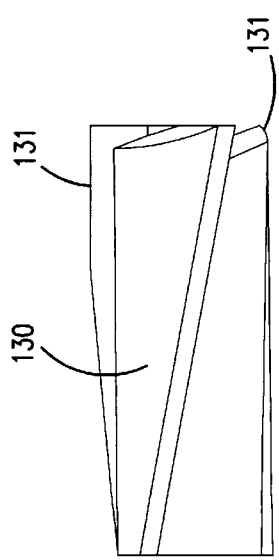

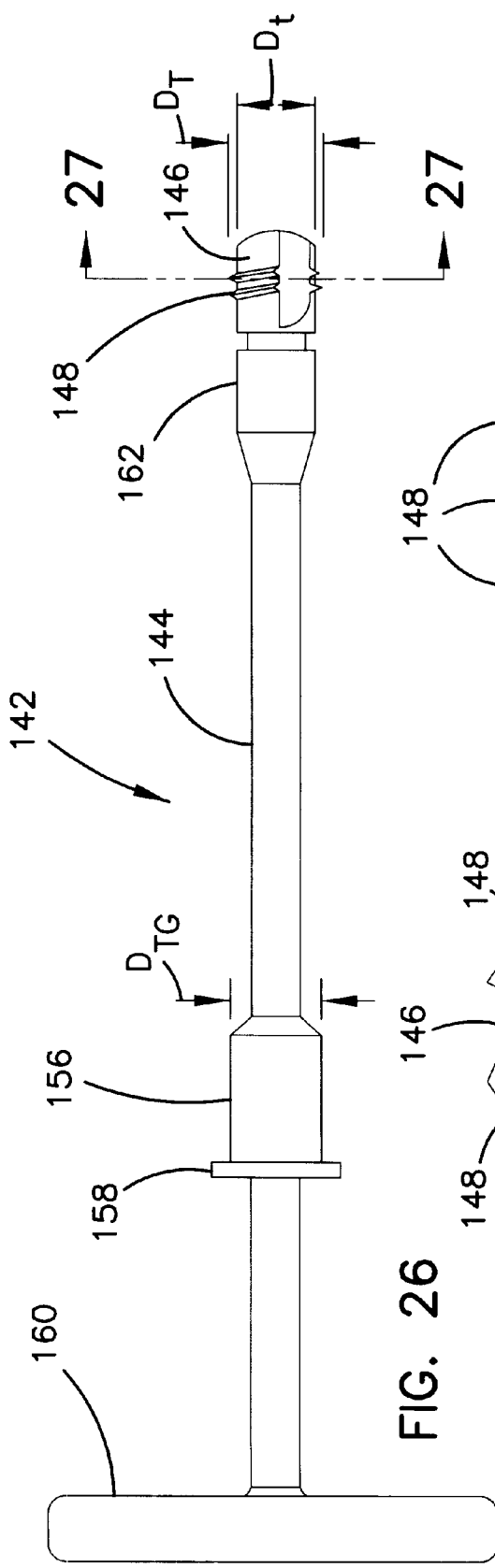
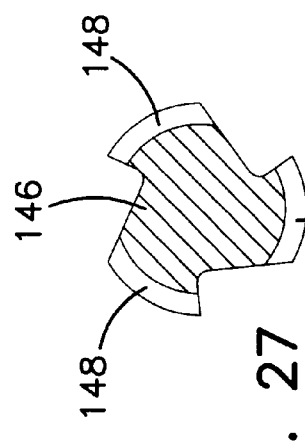
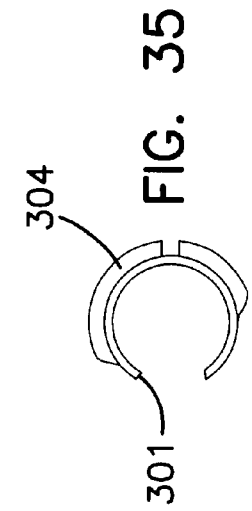
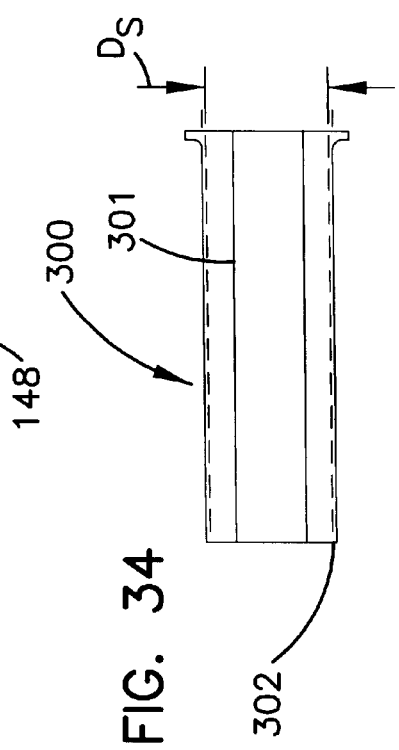
FIG. 26
FIG. 27
FIG. 28
FIG. 34
FIG. 35

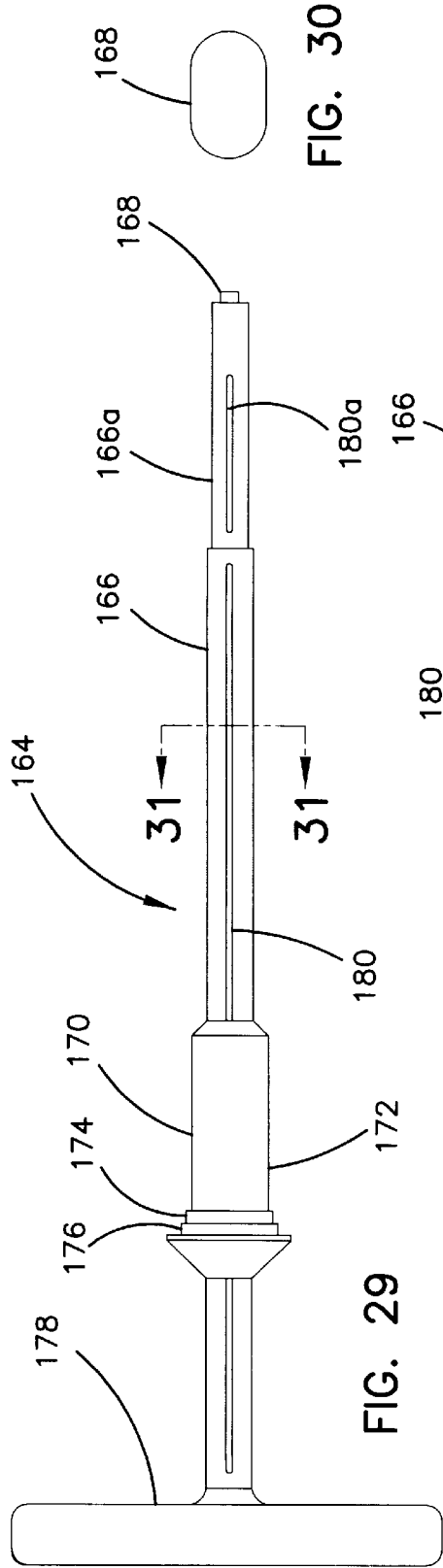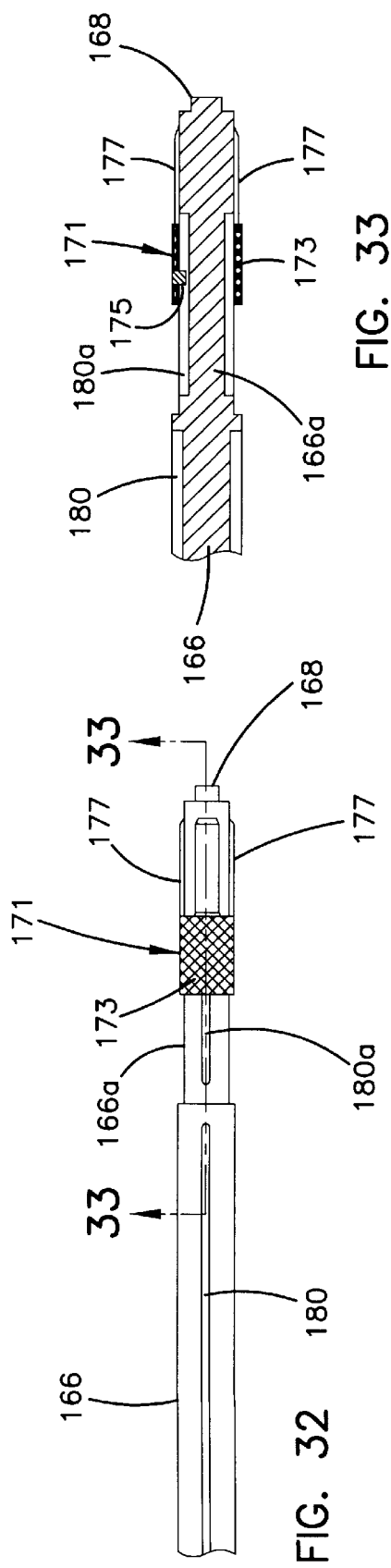

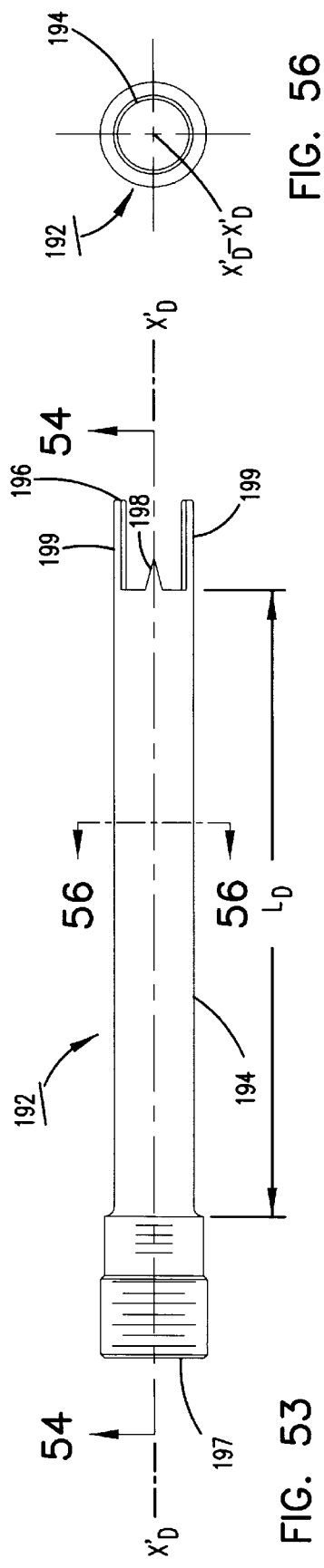
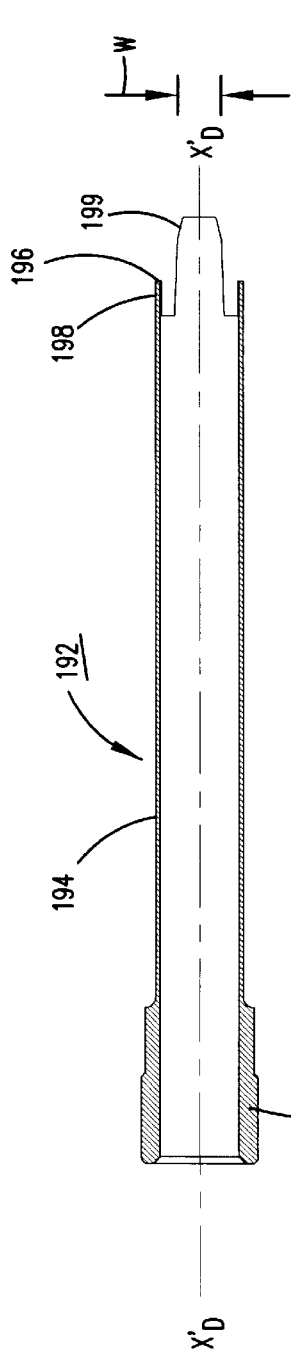
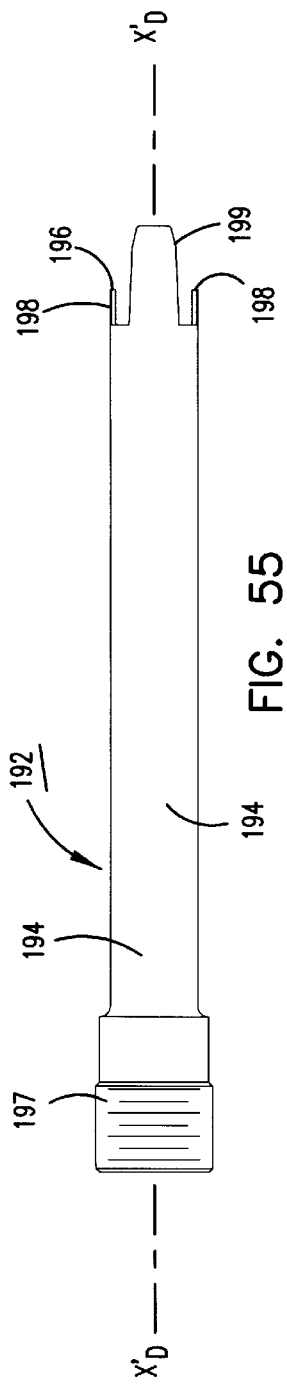
FIG. 53
FIG. 54
FIG. 55
FIG. 56

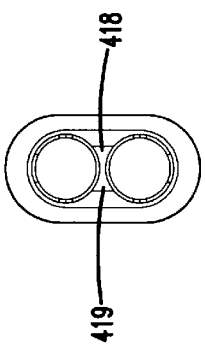
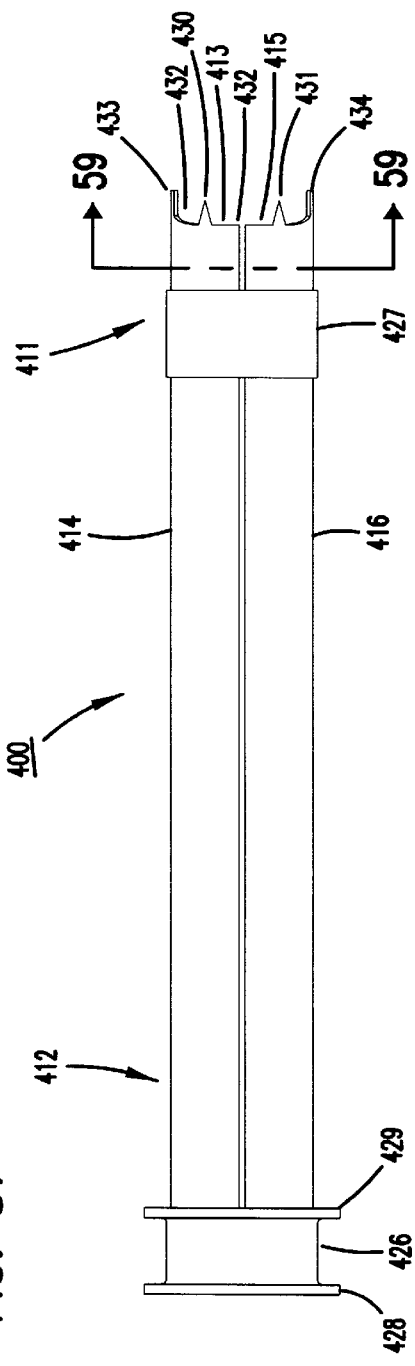
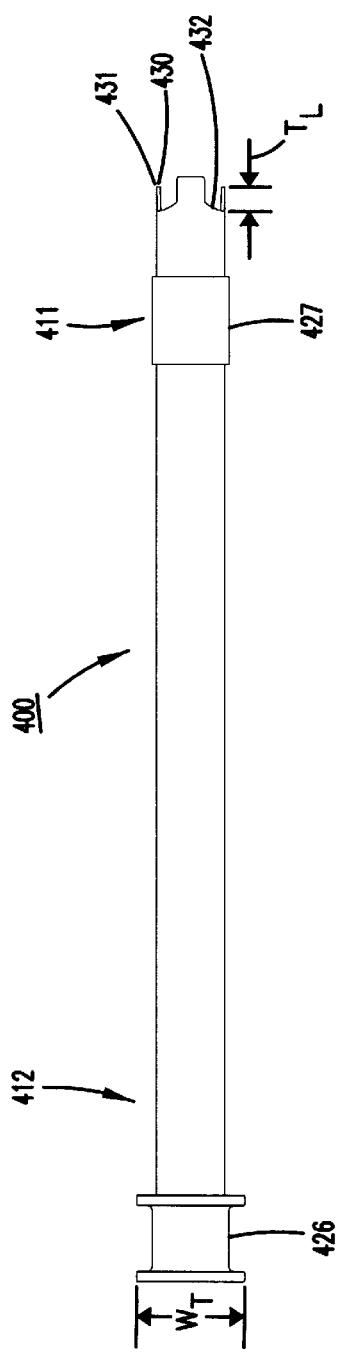

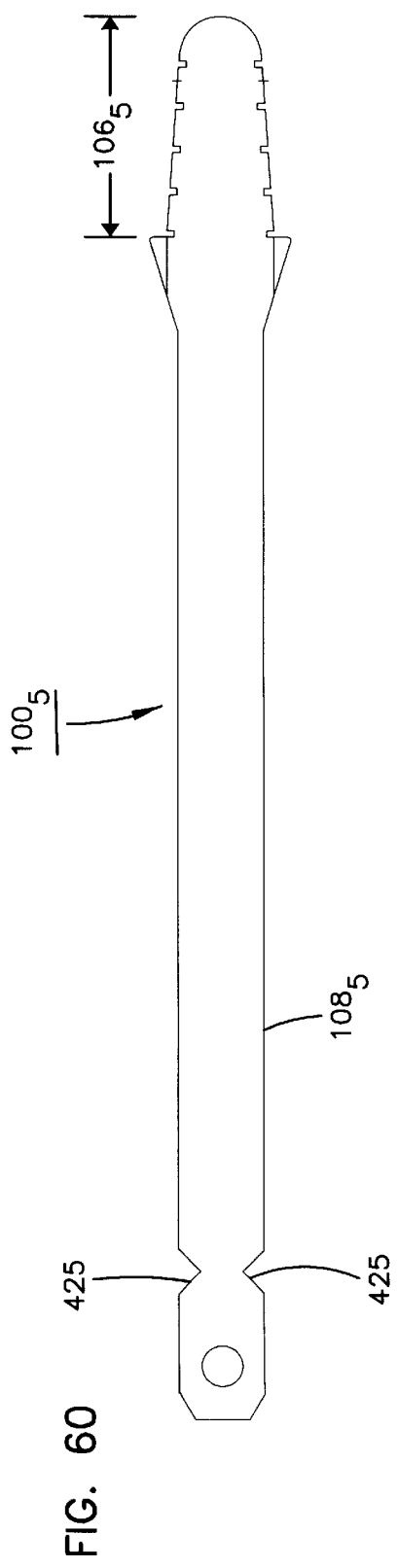
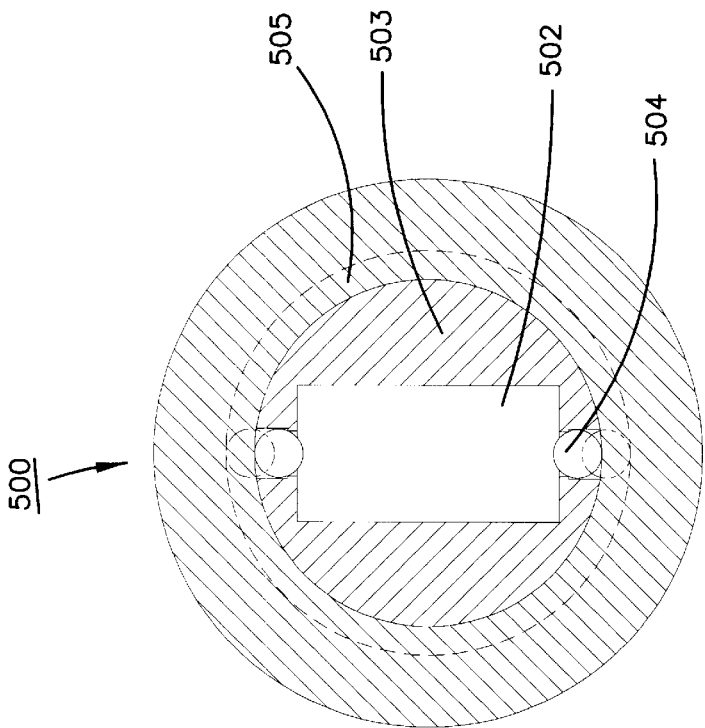
FIG. 60
FIG. 63

APPARATUS AND METHOD FOR SPINAL STABILIZATION

The present application is a continuation-in-part of U.S. Ser. No. 08/921,001, filed Aug. 29, 1997, the entire disclosure of which is incorporated herein by reference.

FIELD OF THE INVENTION

This invention pertains to spinal stabilization surgical procedures and apparatus for performing such procedures. More particularly, this invention pertains to an apparatus and method for implanting a fusion spinal implant between two vertebrae.

BACKGROUND OF THE INVENTION

Chronic back problems can cause pain and disability for a large segment of the population. Frequently, the cause of back pain is traceable to diseased disc material between opposing vertebrae. When the disc material is diseased, the opposing vertebrae may be inadequately supported, resulting in persistent pain.

Surgical techniques have been developed to remove the diseased disc material and fuse the joint between opposing vertebral bodies. Arthrodesis of the intervertebral joint can reduce the pain associated with movement of an intervertebral joint having diseased disc material. Generally, fusion techniques involve removal of the diseased disc, drilling a bore for receiving an implant and inserting the implant between the opposing vertebral bodies.

Spinal fusion implants and related surgical instruments for implanting a fusion device are known and disclosed in, for example, U.S. Pat. Nos. 5,741,253; 5,658,337; 5,609,636; 5,505,732; 5,489,308; 5,489,307; 5,484,437; 5,458,638; 5,055,104; 5,026,373; 5,015,247; and 4,961,740.

Procedures for fusing an intervertebral joint space typically include placement of at least two cylindrical implants in parallel arrangement between the opposing vertebrae. Some presently available systems for implanting fusion devices permit for preparing an implant site through a hollow tube. Procedures for preparing an implant site through a single hollow tube are shown in, for example, U.S. Pat. Nos. 5,505,732; 5,484,437; and 5,489, 307. The disclosure of each of these patents is incorporated herein by reference. In some procedures, the implants are also inserted into the prepared site through the hollow tube. Preparing the implant site by passing instruments through a hollow tube advantageously provides for an isolated surgical field with reduced chance of injury to soft tissues surrounding the surgical site.

However, generally, several steps are required for appropriate placement of the implants using present hollow tube systems. These steps include inserting a spacer into the disc space to distract one side of the intervertebral space, then inserting a second spacer for distracting the second side of the vertebral space, followed by placement of the hollow tube over a guiding mechanism to orient the longitudinal angulation of the implant site. Once the hollow tube is secured in proper alignment, reamers, bores, taps, or other instruments are passed through the hollow tube to prepare the implant site. Either before or after the implant is inserted into the first site, the hollow tube is removed and the procedure is repeated on the opposite side.

Present procedures for placement of an implant through a hollow tube help to reduce the chance of iatrogenic tissue trauma caused by the implant procedure. However, while known procedures provide for reduced chance of injury, the surgeon's accuracy in the relative placement of the hollow tube between the first and second sides is still a matter of guess work and repeated verification using fluoroscopy or radiographic monitoring is needed. Also, the need for separate placement of the hollow guide tube using present methods (i.e., one placement for each implant) increases the possibility for relative misalignment of the implants to occur during insertion.

Thus, there is a continuing need for the precision, safety and ease of placement of spinal fusion implants. The present invention is directed to addressing these needs.

SUMMARY OF THE INVENTION

The present invention increases the ease and enhances the precision of placement of spinal fusion implants between opposing vertebral bodies. Spinal implant procedures using the instrumentation and methods of the invention also reduce the number of steps necessary for implantation.

Throughout the specification, guidance may be provided through lists of examples. In each instance, the recited list serves only as a representative group. It is not meant, however, that the list is exclusive.

In one embodiment, the invention provides a multi-lumen drill tube for preparing a surgical field for a spinal implant. In a preferred embodiment, proper positioning of the multi-lumen drill tube over opposing vertebral bodies is provided by positioning the multi-lumen drill tube relative to an alignment guide centrally positioned within the disc space. According to this embodiment, the multi-lumen drill tube includes a first elongate lumen and a second elongate lumen that are adjacent and parallel to one another. Between the lumens, the multi-lumen drill tube includes a guiding arrangement for receiving the alignment guide positioned between vertebral bodies.

At the distal end, a multi-lumen drill tube can include an anchoring arrangement for securing the multi-lumen drill tube guide to the vertebral bodies. The anchoring arrangement can include teeth which can be embedded into the vertebral body. In addition, the distal end of the guide can include one or more laterally positioned paddles which help reduce the chance of tissues outside the surgical field entering into the surgical field. In a preferred embodiment, one or more of the walls of the multi-lumen drill tube can also include an opening, such as a longitudinal slot, which, in addition to other advantages, facilitates cleaning of the guide.

The multi-lumen tube can be included in a kit comprising implants or additional instruments used for inserting the implants between opposing vertebrae.

The invention also provides a drill depth guide. In one embodiment, the drill depth guide is a spacer cap that can be placed at the proximal end of the multi-lumen drill tube to control the depth of penetration of instruments passed through the multi-lumen drill tube.

The invention also provides a method for implanting a spinal implant into a disc space between opposing vertebral bodies. According to the method, an alignment guide is placed between opposing vertebral bodies at a desired location. The multi-lumen drill tube is then passed over the alignment guide to contact the opposing vertebral bodies. Once in position, the multi-lumen drill tube can be anchored to the vertebral bodies and a site for implanting a fusion device can be prepared through the multi-lumen drill tube.

BRIEF DESCRIPTION OF THE DRAWINGS

FIG. 1 is a side elevation view of a prior art implant for use with the method of the present invention;

FIG. 2 is a view of the implant of FIG. 1 with the implant rotated 90° about its axis;

FIG. 3 is a view taken along line 3—3 of FIG. 1;

FIG. 4 is a view taken along line 4—4 of FIG. 3;

FIG. 5 is a view taken along line 5—5 of FIG. 2;

FIG. 6 is a view taken along line 6—6 of FIG. 3;

FIG. 7 is a side elevation of a first embodiment of a centering guide according to the present invention for use in a posterior approach and without a lordotic distal end;

FIG. 9 is a top plan view of the centering guide of FIG. 7;

FIG. 13 is a side elevation view of a third embodiment of a centering guide according to the present invention for use in an anterior approach and with a lordotic distal end;

FIG. 15 is a top plan view of the centering guide of FIG. 13;

FIG. 16 is a side elevation view of a fourth embodiment of the centering guide according to the present invention for use in a posterior approach and with a lordotic distal end;

FIG. 18 is a top plan view of the centering guide of FIG. 16;

FIG. 19 is a side elevation tube of a prior art drill tube for use with the present invention;

FIG. 20 is a view taken along line 21—21 of FIG. 19;

FIG. 21 is an enlarged side elevation view of a distal end of the drill tube of FIG. 19;

FIG. 22 is a side elevation view of a prior art boring tool for use with the present invention;

FIG. 23 is an elevation view of a proximal end of the boring tool of FIG. 22;

FIG. 24 is an enlarged view of a boring head of the boring tool of FIG. 22;

FIG. 25 is an end elevation view of a distal end of the boring head of FIG. 24;

FIG. 26 is a side elevation view of a prior art tap for use with the present invention;

FIG. 27 is a view taken along line 27—27 of FIG. 26;

FIG. 28 is an enlarged sectional view of threaded cutting teeth on the tool of FIG. 26;

FIG. 29 is a side elevation view of an implant driver for use with the present invention;

FIG. 30 is an end view of a hub on a distal end of the tool of FIG. 29;

FIG. 31 is a view taken along line 31—31 of FIG. 29;

FIG. 32 is a side elevation view of a shaft of a tool of FIG. 29 showing an attachment collet;

FIG. 33 is a cross-sectional view of FIG. 32 taken along line 33—33;

FIG. 34 is a side elevation view of a protective sleeve for use on the drill tube of FIG. 19;

FIG. 35 is an end elevation view of the sleeve of FIG. 34;

FIG. 53 is a side elevation view of an alternative embodiment of a drill tube for use with the centering guide of the present invention;

FIG. 54 is a view taken along line 54—54 of FIG. 53;

FIG. 55 is the view of FIG. 53 with drill tube rotated 90° about its longitudinal axis; and FIG. 56 is a view taken along line 56—56 of FIG. 53.

FIG. 57 is a top plan view of a multi-lumen drill tube according to the invention;

FIG. 58 is a side view of the multi-lumen drill tube of FIG. 57;

FIG. 59 is a cross-section view taken at line 59—59 of FIG. 57;

FIG. 60 is a side elevation view of a fifth embodiment of a centering guide according to the invention for use in an anterior approach and having a lordotic distal end;

FIG. 63 is a transverse cross-section taken at line 63—63 of FIG. 62;

DESCRIPTION OF THE PREFERRED EMBODIMENT

Figure 8:
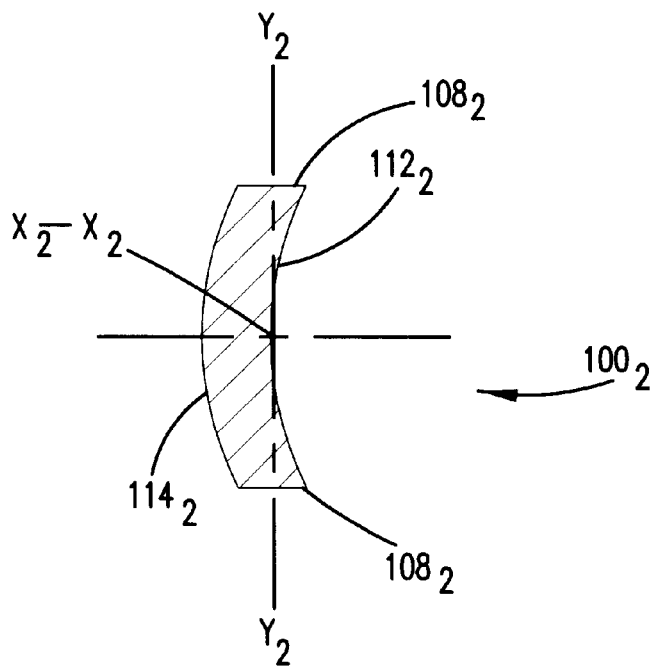
FIG. 8 is a view taken along line 8—8 of FIG. 7.

The instruments and methods of the present invention facilitate the ease and accuracy of placement of multiple spinal implants into a vertebral space between opposing vertebrae. The complementary interaction of the herein disclosed component instruments can also reduce the number of intraoperative images needed to establish the relative alignment of the implants during an implant procedure.

The ability to enhance the accuracy of alignment between two implants inserted into the intervertebral disc space according to the procedures of the invention is facilitated by early establishment and continued maintenance of parallel operating fields at multiple implant sites. Once the surgeon has determined the angular orientation of the implant (e.g., relative to the sagittal and/or transverse plane of the vertebral column), the instrumentation disclosed ensures that the relative positioning of the implants is maintained throughout preparation of the bores that will receive the implants.

A. Implant

Referring to the several drawing figures in which identical elements are numbered identically throughout, a description of the preferred embodiment of the present invention will now be provided. For purposes of illustrating the preferred embodiment, a description of the surgical procedure will be give with respect to an implant 10 such as that shown and described in commonly assigned U.S. Pat. No. 5,489,307. It will be appreciated that the present surgical procedures and apparatuses can apply to a wide variety of implants including threaded implants such as those shown in U.S. Pat. Nos. 5,489,307 and 5,015,247, non-cylindrical implants such as those shown in U.S. Pat. No. 5,609,636 as well as conical implants for use in maintaining a desired lordosis. The term "implant" as used herein may also include bone implants (e.g., autograft, allograft, artificial bone) as well as metallic implants.

The implant 10 (FIGS. 1–6) is a hollow cylinder 12 having male, square-profile threads 14 exposed on the exterior cylindrical surface of cylinder 12. The cylinder includes a forward interior chamber 16 and a rear interior chamber 17 separated by a reinforcing rib 19. A bone slurry or bone chips may be compacted into chambers 16,17.

A first plurality of holes 18 extend radially through the cylinder wall and communicate with the chambers 16,17. A second (and enlarged) plurality of holes 21 are disposed on diametrically opposed sides of the implant 10.

A rear end 22 of the implant has a slot 24 which communicates with the chamber 17. The slot 24 allows the bone slurry or bone chips to be impacted into the implant 10. A slot 25 is defined by rib 19. The slot 25 is sized to receive a distal end of a tool (as will be more fully described) to place the implant within a bore formed between opposing vertebrae. End caps (not shown) may be used with the implant. Such end caps are shown in U.S. Pat. No. 5,489,307.

In a preferred embodiment the technique of the present invention can be performed with a prescribed kit of tools. For the purpose of illustrating the preferred embodiment, the tools of the kit will now be described. It will be appreciated that the method of surgery can be practiced using a wide variety of tools of different size and shapes.

Each of the tools of a kit for performing the surgery as described in this application will be separately described. The use of the tools will become apparent with the description of the method of the invention. Unless otherwise specified, all tools are typically formed of stainless steel.

Since vertebrae size and disc space vary from patient-to-patient (and since such sizes vary along the length of the spine of any give patient), several sizes of implants 10 are anticipated. Presently, implants 10 having minor outside diameters ($D_m$) of 3 mm, 5 mm, 7 mm, 9 mm, 11 mm, 13 mm, 15 mm, 17 mm, 19 mm and 21 mm with lengths (L) of 10 mm, 12 mm, 14, mm 16 mm, 18 mm, 20 mm, 24 mm, 28 mm, 30 mm, 32 mm, 34 mm, 38 mm, 42 mm and 44 mm, respectively, are anticipated to accommodate various spine locations and sizes. The major outside diameters ($D_M$) of the implants 10 are 2.5 mm larger than the minor outside diameters $D_m$.

Several of the tools to be described (e.g., a reaming tool 126) are sized for particular sizes of implants. Namely, the reaming tool 126 must form a bore sized to receive the implant. Since ten sizes of implants are anticipated, ten sizes of boring tools 126 are anticipated as will become apparent to one of ordinary skill in the art.

B. Centering Guide

1. Non-Lordotic Anterior

The present invention utilizes a novel centering guide to ensure accurate positioning of a drill tube prior to forming a bore and placing an implant. With initial reference to FIGS. 10–12, a centering guide 100 is shown for use in an anterior approach where a surgeon is approaching the disc space from an anterior side of the patient.

The centering guide $100_1$ is a rigid rod extending from a distal end $102_1$ to a proximal end $104_1$ along a longitudinal axis $X_1$—$X_1$. The distal end $102_1$ is rounded to facilitate easy insertion of the distal end $102_1$ into the disc space.

The anterior guide $100_1$ has, in cross-section, a major transverse axis $Y_1$—$Y_1$ with the guide being symmetrical about the axis $Y_0$—$Y_0$ and axis $X_1$—$X_1$. At the distal end $102_1$, the guide $100_1$ has a distraction portion $106_1$. The distraction portion $106_1$ is defined by parallel and spaced-apart side edges $108_1$ which are spaced apart by a distance equal to desired distraction of the vertebrae.

The side edges $108_1$ act against the end plates of the opposing vertebrae to urge the vertebrae apart. The end plates hold the centering guide $100_1$ with the axis $X_1$—$X_1$ centrally positioned between the end plates. While the tool proximal end $104_1$ can be moved left or right relative to the vertebrae, the precise central positioning of the proximal end $104_1$ can be determined through x-ray analysis following placement of the centering guide $100_1$ such that a surgeon can be assured that the longitudinal axis $X_1$—$X_1$ extends perpendicular to a transverse plane of the vertebrae.

The distraction portion $106_1$ is provided with a plurality of indicia $110_1$ in the form of grooves positioned at 5 millimeter increments from the distal end $102_1$. The grooves $110_1$ are detectable in x-ray films to permit a surgeon to measure the degree of insertion of the distal end $102_1$ into a disc space. The guide $100_1$ includes a stop $109_1$ on edges $108_1$. The stop $109_1$ abuts vertebrae to prevent further insertion of guide $100_1$ beyond full insertion of portion $106_1$.

Extending between the side edges $108_1$ and extending the length from end $102_1$ to end $104_1$ are left and right (or first and second) guide surfaces $112_1,114_1$. The guide surfaces $112_1,114_1$ are concave and have a radius of curvature equal to a radius of curvature of a drill tube as will be described. While the preferred embodiment of the present invention will be described with reference to using a drill tube having a geometry which is complimentary to the guide surfaces $112_1$, $114_1$, it will be appreciated that the present invention could be performed without a drill tube and by using a drill, tap or other implement to facilitate insertion of an implant where the implement has a curved geometry to match the radius of curvature of the guide surfaces $112_1$, $114_1$ in which case the implement is directly guided by the guide surface, rather than being guided by an intermediate drill tube.

The proximal end $104_1$ is provided with a hole $105_1$ to permit a surgeon to place a tool (not shown) into the hole $105_1$ to twist the centering guide $100_1$ to release the centering guide $100_1$ if necessary. Also, an angled hole $107_1$ is provided near portion $106_1$ to permit insertion of a rod (not shown) into hole $107_1$ to permit a surgeon to force the guide $100_1$ to the mid-line of vertebrae. With the centering guide $100_1$ of FIG. 7 the end plates of the vertebrae will be distracted in parallel spaced apart relation since the side walls $108_1$ are parallel at the distraction portion $106_1$.

2. Non-Lordotic Posterior

Figure 12:
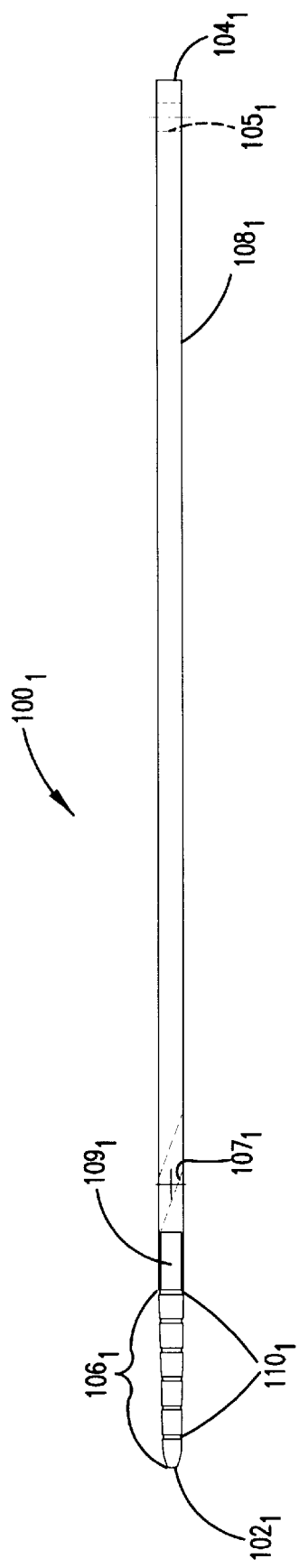
FIG. 12 is a top plan view of the centering guide of FIG. 10.
Figure 10:
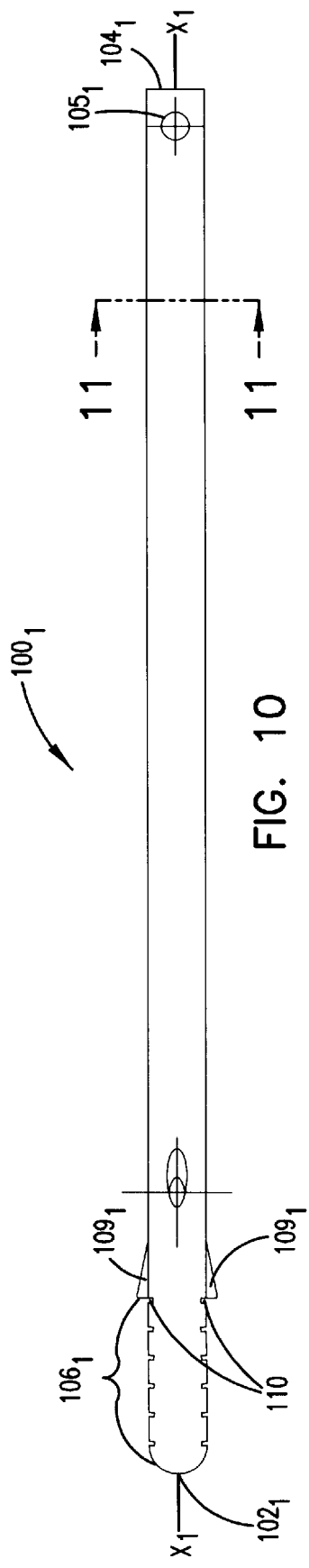
FIG. 10 is a side elevation view of a second embodiment of a centering guide according to the present invention for use in an anterior approach and without a lordotic distal end.
Figure 11:
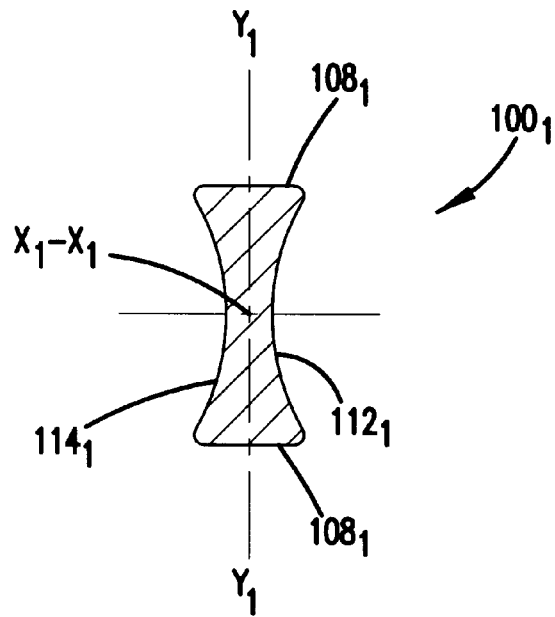
FIG. 11 is a view taken along line 11—11 of FIG. 10.

FIGS. 7–9 show a centering guide $100_2$ similar to that of FIGS. 10–12 but differing due to the fact that centering guide $100_2$ of FIGS. 7–9 is intended for use in a posterior approach where a surgeon approaches the vertebrae from the posterior side of the patient. In the embodiments of FIGS. 7–18, similar elements are numbered similarly with the addition of subscripts to distinguish the embodiments.

Like the centering guide $100_1$ of FIGS. 10–12, the centering guide $100_2$ of FIGS. 7–9 is for a non-lordotic parallel distraction appliance where the side edges $108_2$ are spaced apart in parallel alignment at the distraction portion $106_2$. Unlike the centering guide $100_1$ of FIGS. 10–12, the centering guide 1002 of FIGS. 7–9 is not symmetrical about its major transverse axis $Y_2$—$Y_2$ (although it is symmetrical about axis $X_2$—$X_2$. Instead, the centering guide $100_2$ of FIGS. 7–9 includes only a first concave guiding surface $112_2$ extending on one side of the centering guide $100_2$. The opposite surface $114_2$ is a convex surface to present a smooth surface opposing a dura following insertion of the centering guide $100_2$ as will be described.

3. Lordotic Posterior

The centering guides $100_1,100_2$ of FIGS. 7–12 both show distraction portions $106_1,106_2$ having distracting edges $108_1,108_2$ which are parallel and spaced apart. From time to time, it may be desirable to ensure that end plates of opposing vertebrae are retained at a desired degree of lordosis (i.e., with a non-parallel angle between end plates of the opposing vertebrae).

Figure 17:
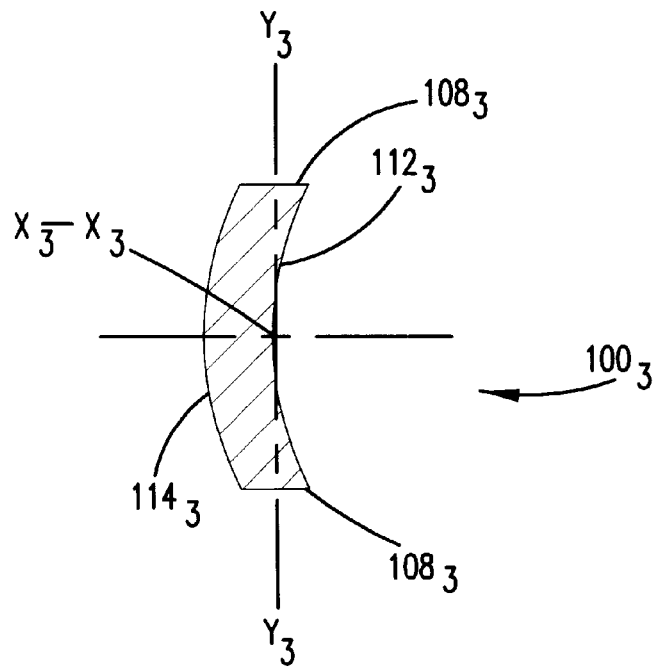
FIG. 17 is a view taken along line 17—17 of FIG. 16.

FIGS. 16–18 show a centering guide $100_3$ for a posterior approach and having a lordotic distraction portion $106_3$. The distraction portion $106_3$ has side edges $108_3$ placed at an angle, A, equal to the desired degree of lordosis. In all other respects, the centering guide $100_3$ of FIGS. 16–18 is identical to that of FIGS. 7–9.

4. Lordotic Anterior

Figure 14:
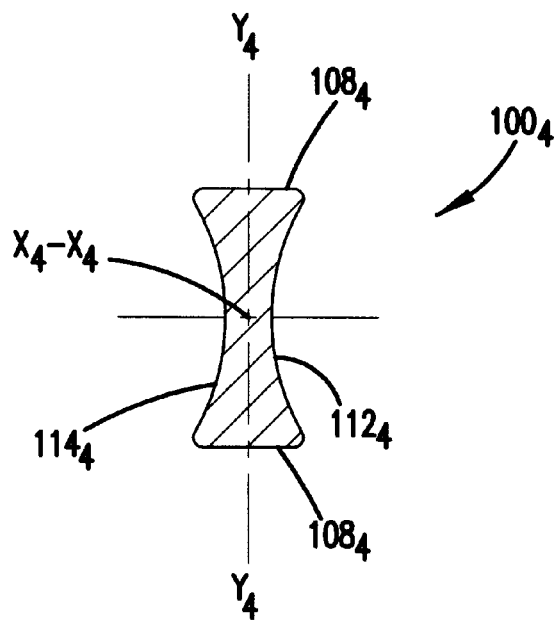
FIG. 14 is a view taken along line 14—14 of FIG. 13.

FIGS. 13–15 show a lordotic centering guide $100_4$ for use in an anterior approach. The distracter end $106_4$ of the tool $100_4$ has distracting side edges $108_4$ set at a lordotic angle, A', equal to but reverse that of the embodiment of FIGS. 16–18. In all other respects, the centering guide $100_4$ of FIGS. 13–15 is identical to that of FIGS. 10–12.

5. Laparoscopic

Laparoscopic versions of both the lordotic and non-lordotic centering guides can also be provided. Although not shown in the drawings, such laparoscopic centering guides would have a shorter length than the non-laparoscopic centering guides shown in the drawings. For example, a non-lordotic, laparoscopic anterior centering guide would be identical to that of guide $100_1$ (FIG. 10) but have its axial length detachable so that the terminal end $104_1$ is spaced from the distal tip $102_1$ by about 3 inches. After insertion of the portion $106_1$ into the disc space, approximately 1.5 inches of the guide surfaces $112_1$, $114_1$ would protrude beyond the vertebrae and provide a guide surface for directing a laparoscopic drill tube. The design would also permit the maintenance of insufflation.

C. Drill Tube

In one embodiment, a drill tube 92 (FIGS. 20–22) is provided in the form of a hollow cylindrical tube 94. The distal end 96 of the tube 94 is provided with axially projecting teeth 98. The proximal end 99 of the tube 94 is flared outwardly. As will be apparent, ten sizes of tube 92 are required with inside diameters $D_{DT}$ to slip in close tolerance over ten sizes of implants 10 (i.e., $D_{DT}$ is 0.5 mm larger than $D_M$).

The teeth 98 each have a length, $T_L$, of preferably 3 mm. The valleys 97 are flat to provide stop surfaces to hit bone as teeth 98 are forced into vertebrae. This helps prevent the drill tube 92 from being forced too far into bone. The drill tube 92 is identical to that shown in U.S. Pat. No. 5,489,307.

An alternative embodiment of a drill tube 192 is illustrated in FIGS. 53–56. The drill tube is a hollow cylindrical tube 194 with an outside diameter having a radius of curvature to match the radius of curvature of the guide surfaces $112_1$, $114_1$. The distal end 196 of the tube 194 includes diametrically opposed and axially projecting sharpened teeth 198 for penetration into vertebrae. Diametrically opposed and axially extending retraction paddles 199 are provided ninety degrees offset from the teeth 198 (with reference to the longitudinal axis ($X'_D$—$X'_D$). The paddles 199 have a width (W in FIG. 54) equal to the desired distraction of the vertebrae. The proximal end 197 of the tube 194 is a handle to be gripped by a surgeon. The tube 194 has a length $L_D$ measured from the base of the teeth 198 and retraction paddles 199 to the base of the handle 197. The length $L_D$ is equal to the length of a centering guide (such as the length of guide $100_1$ of FIG. 10) between the proximal end $104_1$ and the insertion portion $106_1$. Therefore, when the insertion portion $106_1$ is fully inserted into the disc space, the end $104_1$ buts against the handle 197 when the teeth 198 are forced into the vertebrae.

D. Vertebral Reamer

A vertebral reamer 126 (or boring tool) (FIGS. 22 through 25), is provided for forming a bore. The reamer 126 is such as that shown in U.S. Pat. No. 5,489,307. The reamer 126 includes a shaft 128. A distal end of the shaft is provided with a reamer end 130 having side and end cutting blades 131. A proximal end of the shaft is provided with an outwardly flared hub 132. Extending from hub 132 is an axial shaft 134. For ten sizes of implants 10, ten sizes of reamers 126 are required with the kit. The outside diameter DR of reamer 126 equals the minor outside diameter $D_m$ of implants 10. The diameter $D_{RG}$ of the guide hub 133 equals the inner diameter of the drill tube $D_{DT}$.

E. Bonetap

In the event a threaded implant is utilized (as is the case in the preferred embodiment of the present invention), the bores for the implants are partially pre-threaded. To pre-thread, a bone tap 142 (FIGS. 26–28) is provided, having a shaft 144. The tap 142 is such as that shown in U.S. Pat. No. 5,489,307. At the distal end of the shaft 144 is a tapping head 146 having tapping threads 148. Near the proximal end of the shaft 144 is an enlarged diameter portion 156 having an outwardly flared flange 158. A handle 160 is secured to an enlarged portion 156. The shaft 144 is also enlarged at portion 162 adjacent tapping head 146. The enlarged portion 156 is sized with diameter $D_8$ to be received, in close tolerance, within the drill tube 92 such that the tube 92 will guide the tap 142 as will be more fully described.

Since ten sizes of implants 10 are intended to be utilized, ten sizes of bone taps 142 are required. Diameter $D_T$ is equal to the major outside diameter $D_M$ of implant 10. The head 146 has a minor outside diameter $D_t$ (i.e., the diameter without threads 148) equal to the minor outside diameter $D_m$ of the implants 10.

F. Implant Driver

To place implant 10, an implant driver 164 (FIGS. 29 through 33) is provided. The driver 164 is such as that shown in U.S. Pat. No. 5,487,307. A driver is also shown in U.S. Pat. No. 5,609,636. The driver 164 includes a shaft 166 having a reduced diameter distal portion 166a. A distal end of the shaft 166 is provided with a hub 168 sized to be received within slot 24 of the implant 10 to urge the implant 10 to rotate as the implant driver 164 is rotated. The implant driver 164 includes a stepped enlarged portion 170 including a first diameter portion 172, a second diameter portion 174 and a third diameter portion 176 to accommodate the different diameters of drill tubes 92. A handle 178 is secured to the shaft 164. Grooves 180,180a are formed on the shafts 166,166a and extend along their axial lengths. The grooves 180 provide a means for a surgeon to sight the alignment of the implant.

FIGS. 32-33 show the implant driver 164 with a collet 171. The collet 171 has a cylindrical, knurled body 173 slidably carried on shaft 166a. A pin 175 extending from body 173 into groove 180a permits collet 171 to slide on shaft 166 but not rotate. Four prongs 177 extend axially from body 173 toward hub 168.

Figure 46:
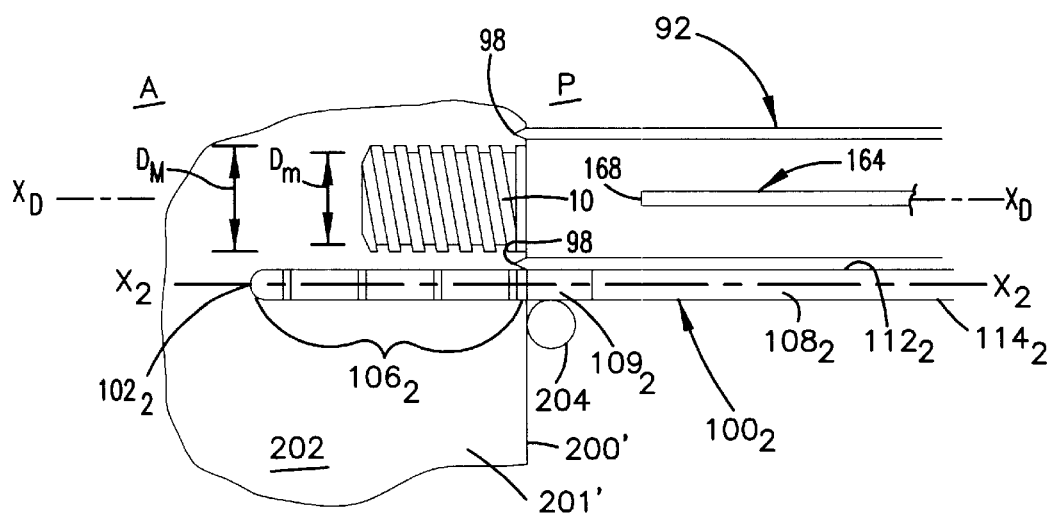
FIG. 46 is the view of FIG. 45 showing an implant inserted into the threaded bore of FIG. 45 and showing removal of the implant driving tool through the drill tube.

In use, shaft 166 is passed through end opening 24 of implant 10. Hub 168 is received within slot 25. The prongs 177 are forced by a surgeon pushing on body 171 for the prongs 177 to be urged between opposing surfaces of the implant 10 and shaft 166a to thereby securely capture the implant 10 on driver 164. As a result, the implant 10 cannot inadvertently fall off. (For ease of illustration, the Figures showing the method of the invention, e.g., FIG. 46, does not show use of collet 171).

G. Drill Tube Sheath

Drill tube 92 is passed through a patient's body to an implant site. To avoid risk of teeth 98 damaging vessels, nerves or organs, a drill tube sheath 300 is provided (FIGS. 34,35). The sheath 300 is such as that shown in U.S. Pat. No. 5,489,307. The sheath 300 is a hollow tube with inside diameter $D_S$ slightly smaller than the outside diameter of drill tube 92 (accordingly, ten sizes of sheath 300 are required). The sheath 300 has an axial slit 301 extending its entire length. The sheath 300 has a blunt distal end 302 and a flared proximal end 304.

The sheath is slipped onto the drill tube 92 with end 302 extending beyond the teeth 98. As the drill tube 92 is passed to an implant site the blunt end 302 covers the teeth and prevents the unwanted cutting of vessels, nerves or organs. When pressed against vertebrae, the end 302 abuts the vertebrae. With continued advancement of the tube 92 toward the vertebrae, the sheath 300 slides on the tube 92 until teeth 98 abut the vertebrae.

In the method of the invention, sheath 300 remains in place whenever drill tube 92 are used. However, for ease of illustration, sheath 300 is not shown in FIGS. 42–50.

H. Posterior Technique

The present invention will first be described with reference to use in a posterior approach. In a posterior approach, a surgeon seeks access to the spine through the back of the patient. Another alternative approach is the lateral approach, where the patient is on his side and a single cage is inserted across the disc space. An alternative approach is an anterior approach where the surgeon seeks access to the spine through the abdomen of a patient. The approaches can be done through open surgery or through laparoscopic surgery.

While a posterior approach will be described in detail, it will be appreciated that the present invention can be used in an anterior or lateral approach for both laparoscopic or non-laparoscopic procedures.

Figure 36:
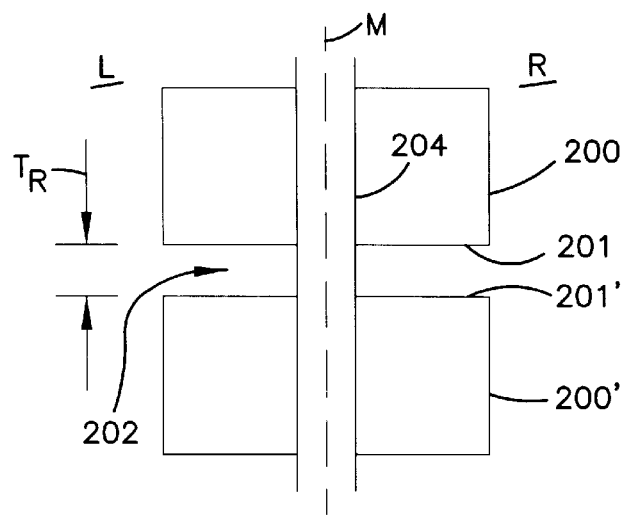
FIG. 36 is a schematic posterior to anterior view of two vertebrae separated by a disc space and showing a dura extending centrally along a mid line between the vertebrae.

With initial reference to FIG. 36, once a surgeon has identified two vertebrae 200,200' which are to be fused together, the surgeon identifies an implant 10 of desired size and the surgeon determines the desired amount of distraction of the disc space 202 to be required before placement of the implant 10. In selecting the implant size, the surgeon should ensure that the device will remain within the lateral borders of the intervertebral disc space 202 while also penetrating at least 3 mm into the vertebral bodies 200,200' cephalad and caudal to the disc.

In the posterior technique, a patient is placed on the operating table in either a prone or kneeling-sitting position. At the discretion of the surgeon, the spine is flexed slightly. Anesthesia is administered.

Exposure of the intervertebral disc is obtained through any suitable technique well-known in the art. The facet of the vertebrae is removed in as limited amount as possible to permit insertion of the instruments and the implants. Preferably, bone dissected from the lamina, facets and spinous process are preserved for later use as bone graft.

FIG. 36 shows two vertebrae 200,200' separated by a disc space 202. For ease of illustration, disc material is not shown in space 202 having an undistracted thickness $T_R$. In the posterior P to anterior A view, a dura 204 extends between the vertebrae 200,200' and is centrally positioned along a medial line, M, between the vertebrae 200,200'. The line M separates the disc space 202 and vertebrae 200,200' into a left side L and right side R corresponding to the patient's left and right sides.

Figure 37:
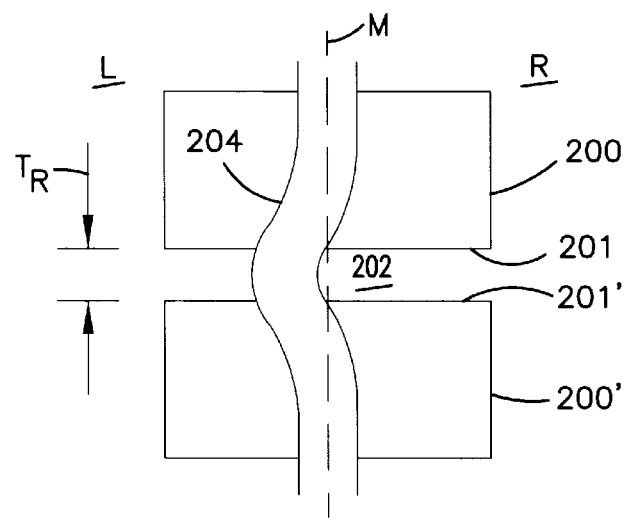
FIG. 37 is the view of FIG. 30 with a dura retracted to a left side.
Figure 38:
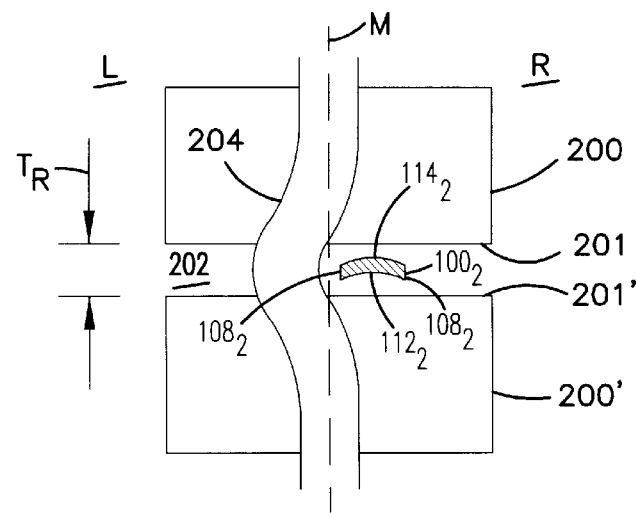
FIG. 38 is the view of FIG. 37 with a centering guide of the present invention such as that shown in FIG. 7 inserted into the disc space between the vertebrae prior to the centering guide being rotated to a distraction position.

As shown in FIG. 37, the dura 204 is first retracted to the left through any suitable means to expose the disc space 202 and vertebrae 200,200' at the medial line, M. A distal end $102_2$ of the centering guide $100_2$ of FIGS. 7–9 is inserted into the disc space 202 in the manner illustrated in FIG. 38 with the distracting side edges $108_2$ opposing and in line with the disc space 202.

Figure 39:
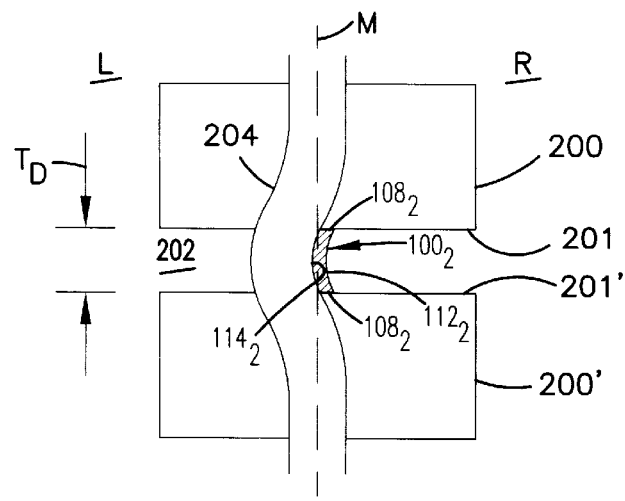
FIG. 39 is the view of FIG. 38 with the centering guide rotated to a distraction position.
Figure 40:
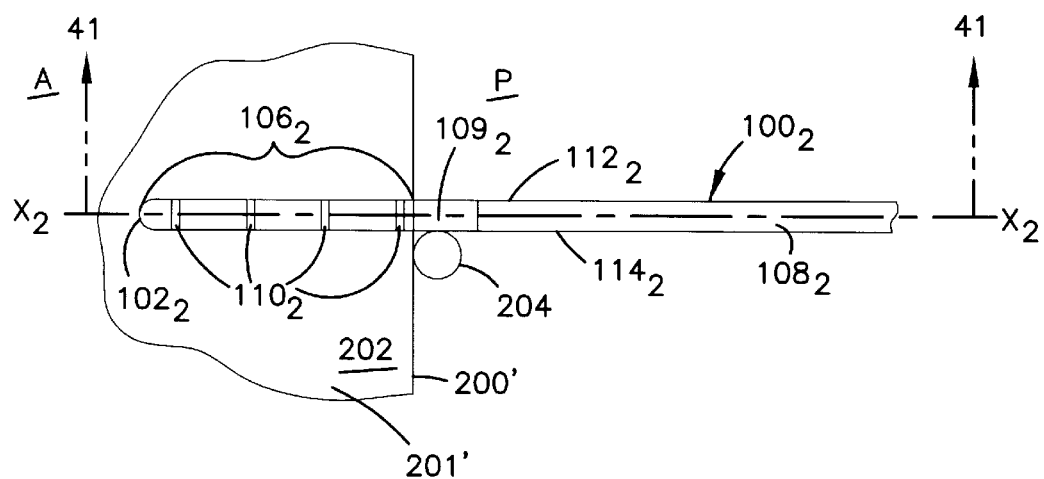
FIG. 40 is a plan view of a disc space showing the elements of FIG. 39.
Figure 41:
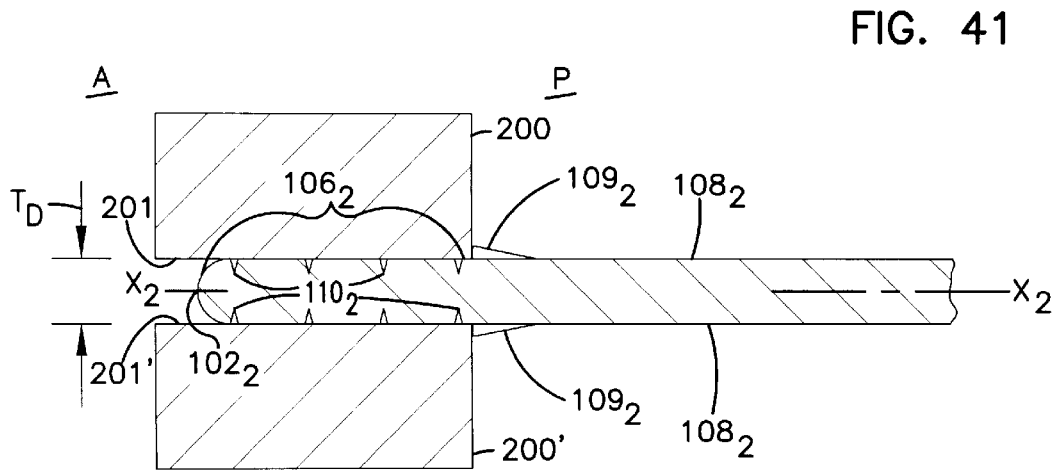
FIG. 41 is a view taken along line 41—41 of FIG. 40.
Figure 42:
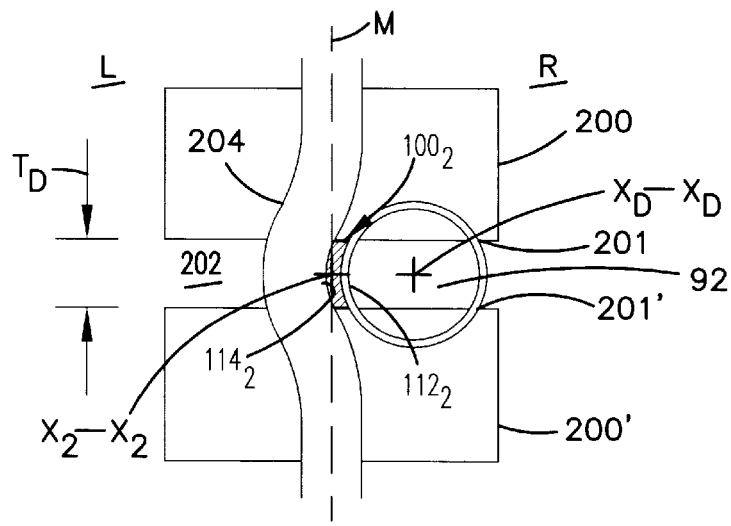
FIG. 42 is the view of FIG. 39 with a drill tube of FIG. 19 inserted into position and guided by the centering guide.
Figure 43:
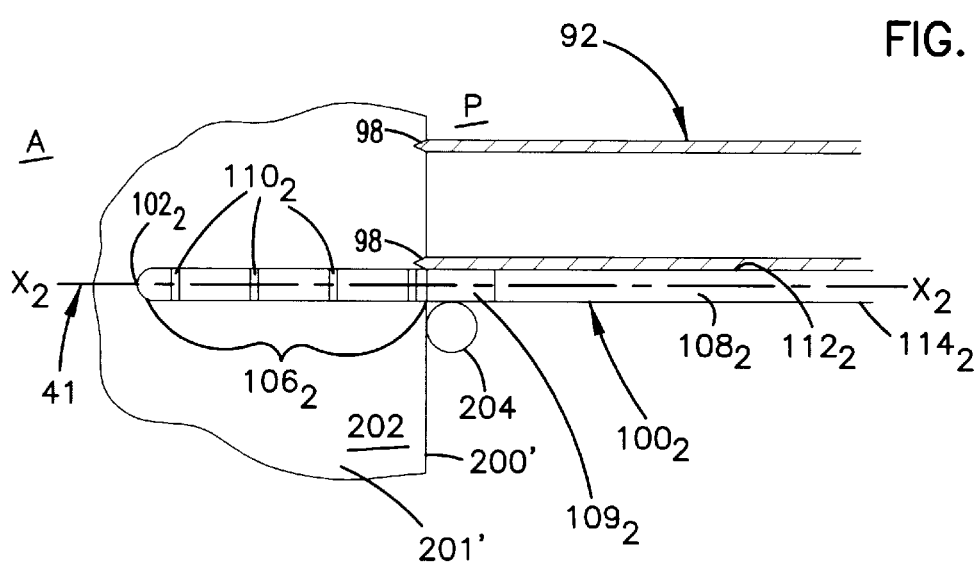
FIG. 43 is a plan view of the elements of FIG. 42 with the drill tube shown in section.

After initial insertion of the distal end $102_2$ into the disc space, the centering tool $100_2$ is rotated 90° to the position shown in FIG. 39 such that the side edges $108_2$ of the distraction portion $106_2$ oppose and distract the vertebrae and the convex surface $114_2$ is opposing the dura 204 to prevent damage to the dura 204. The vertebrae 200,200' are now distracted to a spacing of TD equal to the distance between side edges $108_2$.

The distraction portion $106_2$ of the guide $100_2$ is forced into the disc space 202 at the mid line M of the disc space 202. The size (i.e., the spacing between the side edges $108_2$) of the centering guide $100_2$ is selected to distract the annulus fibroses without causing damage to the surrounding vertebral bone, annular fibers or spinal nerves. Accordingly, it is recommended that a surgeon initially insert a relatively narrow distal end centering guide (6 millimeters) followed by successively larger guides until the annulus is distracted to the surgeon's satisfaction.

Once the correct maximum size distraction portion $106_2$ has been chosen, it is left in place. The disc space 202 has now been stretched so that a parallel distraction of the end plates 201,201' of the vertebrae 200,200' has occurred on both the left and right sides of the vertebrae. The distraction portion $106_2$ is fully inserted such that the indicia $110_2$ are flush or slightly recessed within the disc space.

Following placement of the distracting centering guide $100_2$, the drill tube 92 is placed against the centering guide $100_2$. Since the guiding surface $112_2$ of the centering guide $100_2$ is concave with a radius of curvature matching the outer radius of curvature of the drill tube 92, the drill tube 92 can be slid along the length of the guide $100_2$ into precise position with the axis $X_D$—$X_D$ of the drill tube 92 centrally positioned between the end plates 201,201' of the vertebrae 200,200'.

In a preferred embodiment, the drill tube 92 will be surrounded by a sliding protective sleeve 300 such as that shown in FIGS. 34–35 and described fully in U.S. Pat. No. 5,489,307. The thin wall of the drill sleeve 300 has substantially the same radius of curvature as the drill tube 92 and does not materially affect the positioning. At most, the addition of the protective sleeve 300 increases the spacing of the axis $X_D$—$X_D$ of the drill tube 92 from the axis $X_2$—$X_2$ of the guide $100_2$ (FIG. 51) but does not alter the central positioning of the axis $X_D$—$X_D$ of the drill tube 92 between the end plates 201,201'. For ease of illustration, the drill sleeve protective sleeve is not shown in FIGS. 42–50.

Figure 44:
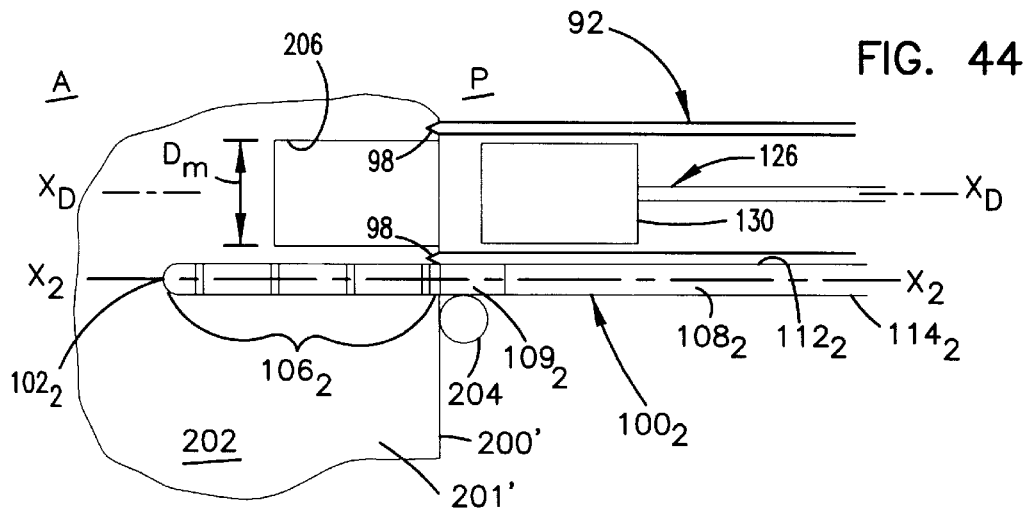
FIG. 44 is the view of FIG. 43 following formation of a bore in the disc space and vertebrae and showing retraction of a boring tool through the drill tube.

With the drill tube 92 in place, the preparation of the implant bore 206 is completed by inserting the reamer 126 into the drill tube 92 (FIG. 44). The reamer 126 is rotated with any suitable driver (such as driver 136 shown in U.S. Pat. No. 5,489,307).

Since the drill tube 92 is centrally placed with the axis $X_D$—$X_D$ of the drill tube 92 centrally positioned between the end plates 201,201', the reamer 126 will bore into the disc space 202 and bore equally into and through the end plates 201,201' of the opposing vertebrae. The reamer 126 is selected to form a bore 206 having a diameter $D_m$ equal to the minor outside diameter of the implant 10 (in the case of a cylindrical implant such as that shown in FIGS. 1–6).

Figure 45:
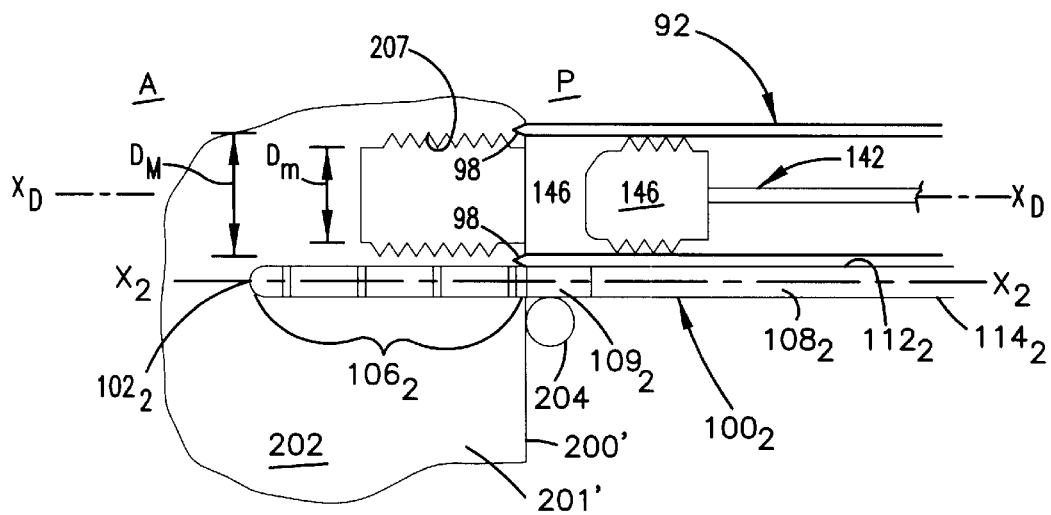
FIG. 45 is the view of FIG. 44 following formation of a tapped thread in the bore of FIG. 44 and showing removal of the tapping tool through the drill tube.

For use with a threaded implant 10 such as that shown in FIGS. 1–6, a bone tap 142 is passed through the drill tube 92 and rotated to at least partially pretap the bore (FIG. 45). The tap is then removed to expose a tapped bore 207 with the drill tube 92 remaining in place. The implant 10 may then be packed with a bone graft material. The graft may be autograft obtained previously from the iliac crest or some other graft material (e.g., allograft or artificial bone). The implant 10 is attached to the implant driver 164 by placing the hub 168 within the slot 25 and securing the implant 10 with the collet 171. The implant 10 is then passed through the drill tube 92. The implant 10 is threaded into the bore 207 with the implant driver 164 by the surgeon rotating the driver 164 and advancing it into the drill tube 92. As disclosed in U.S. Pat. No. 5,489,307, it is desirable that the larger holes of the implant are oriented in a superior-inferior direction (i.e., the larger holes are facing the vertebrae 200,200').

Figure 47:
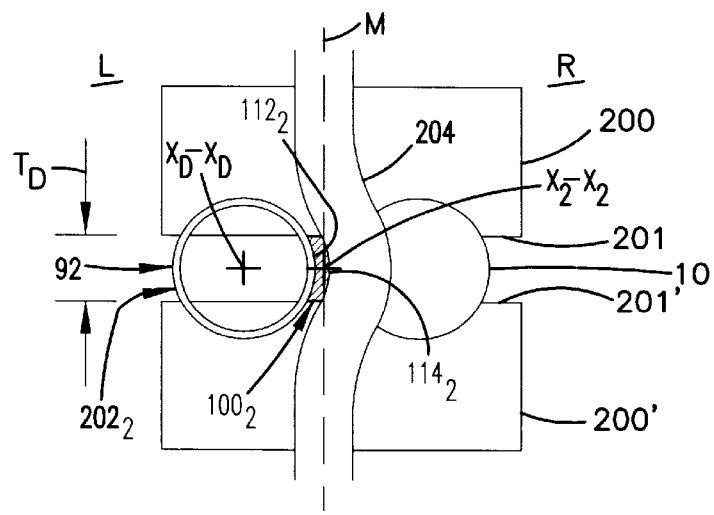
FIG. 47 is a posterior-to-anterior view showing a dura retracted to a right side over an inserted implant and with the centering guide reversed and with a drill tube positioned against the centering guide prior to formation of a bore on the left side of the vertebra.
Figure 48:
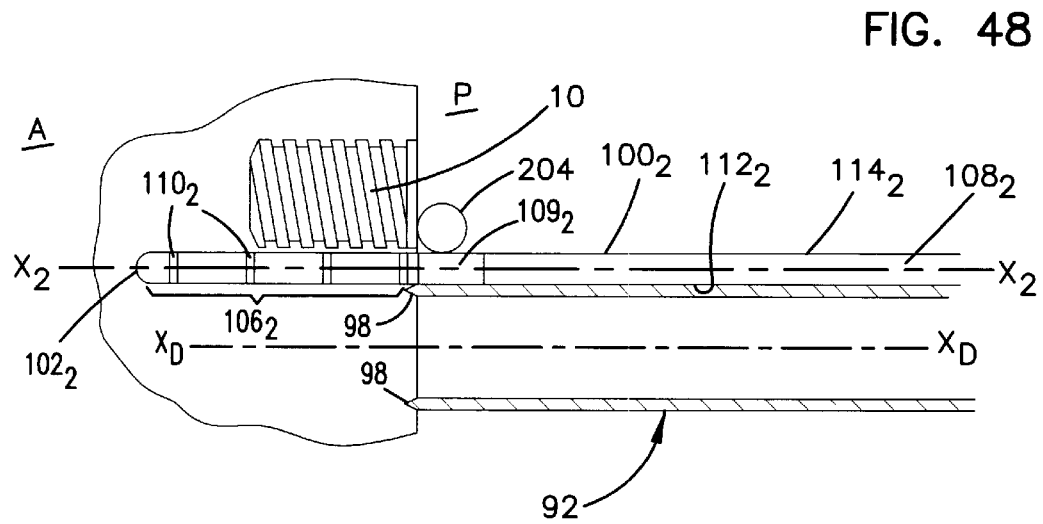
FIG. 48 is a plan view of the elements of FIG. 47 with the drill tube shown in section.
Figure 49:
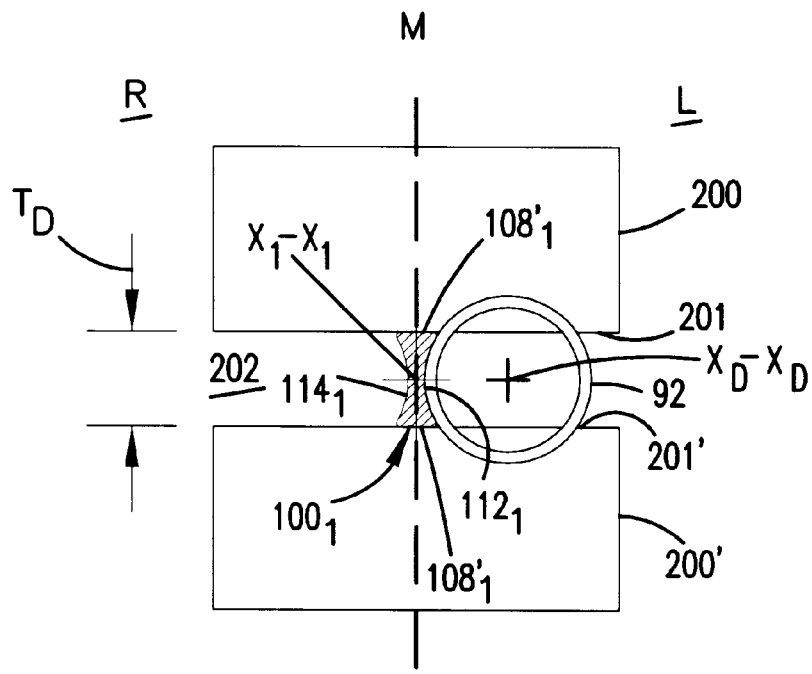
FIG. 49 is an anterior-to-posterior view of two vertebrae separated by a disc space and showing a non-lordotic, anterior approach centering guide of the present invention (such as that shown in FIG. 10) and shown inserted into the disc space between the vertebrae and with a drill tube being guided by the centering guide.

After the implant 10 is fully in place, the implant driver 164 is removed through the drill tube 92 (FIG. 47). The drill tube 92 is then removed. The dura 204 is retracted slightly and the centering guide 100 is then removed. The dura 204 is then retracted to the opposite side and the centering guide 1002 is repositioned with the disc space 204 but rotated 180° relative to FIG. 39 so that the rounded side $114_2$ is facing both the dura 204 and the previously placed implant 10 and the guide surface $112_2$ is facing the opposite side of the disc space 202. The procedure can then be repeated by placing the drill tube 92 against the vertebrae with the drill tube 92 aligned by the guide $100_2$ as previously described (FIG. 47).

The foregoing discussion illustrates the use and method of an apparatus of the invention in a posterior approach. It will be noted that for placing two implants 10, the centering guide $100_2$ is removed and reinserted into the disc space 202 to reorient the guiding surface $112_2$.

I. Anterior Approach

Figure 50:
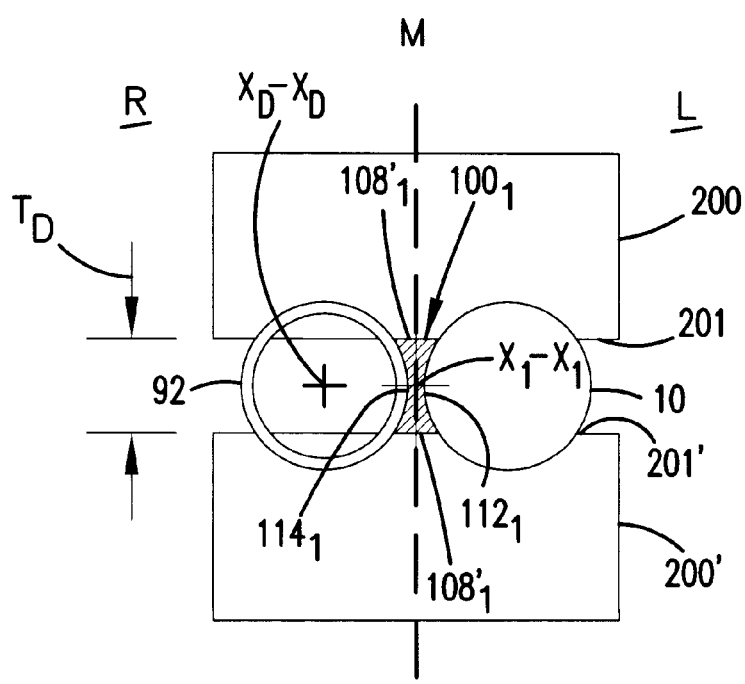
FIG. 50 is the view of FIG. 49 showing an implant inserted into a formed bore on a left side of the vertebrae and with the drill tube moved to be guided by an opposite side of the centering guide prior to formation of a bore on the right side of the vertebra.
Figure 51:
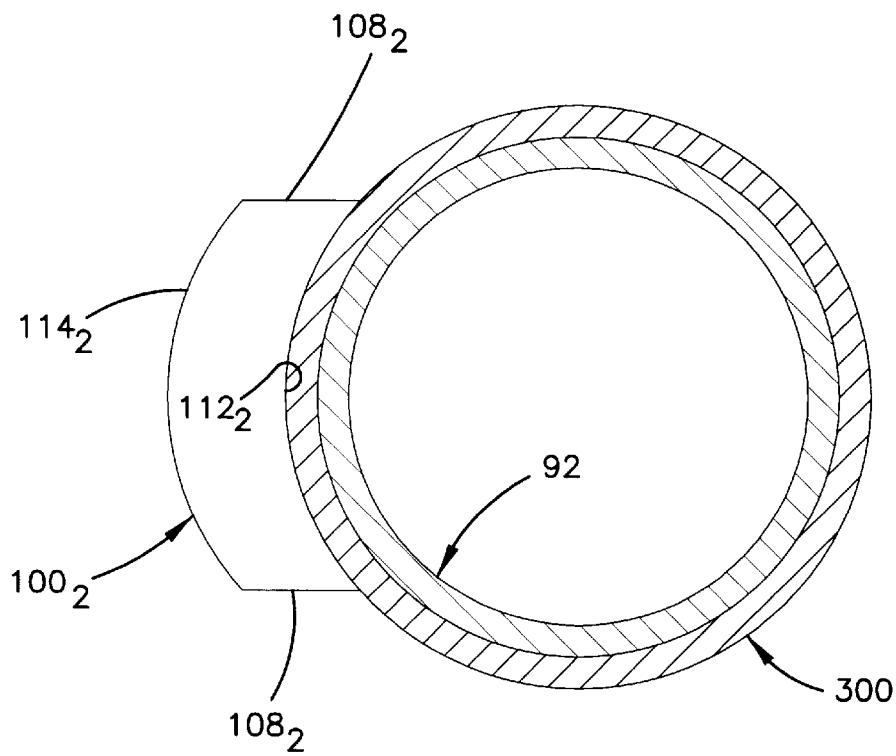
FIG. 51 shows a drill tube of FIG. 19 and a protective sleeve of FIG. 34 guided by a posterior centering guide of FIG. 7.
Figure 52:
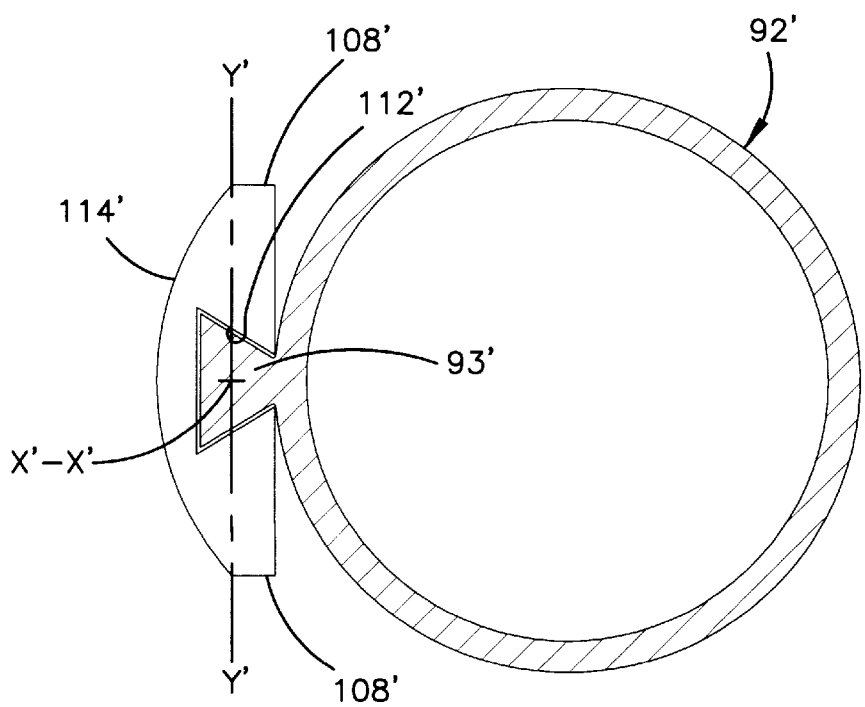
FIG. 52 shows a still further embodiment of a centering guide.

When performing an anterior approach, the surgeon uses the anterior guide $100,100_4$ which has concave guiding surfaces 112,114 on opposite sides of the centering guide 100. With such structure, the anterior centering guide 100 is placed at the mid line M and a drill tube 92 is guided by a first 112 of the guiding surfaces 112,114 so that a first bore can be formed, tapped and an implant 10 inserted through the drill tube (FIG. 50). After the implant 10 is inserted, the centering guide 100 remains in place but the drill tube 92 is moved to the opposite side and guided into position by the second guiding surface 114 (FIG. 51). With the drill tube 92 in position on the second side, a bore 206 is then formed by passing the reamer and tap through the drill tube and a second implant is inserted through the drill tube.

J. Lateral Approach

The present invention is particularly suited for a lateral approach where an elongated single implant is to be placed in the inner vertebral space. The present invention requires smaller access space to the disc space which is of particular advantage in a lateral approach where there is substantial anatomic structure limiting access to the disc space in a lateral approach at certain vertebrae locations.

K. Additional Embodiments

In the foregoing description, the guide surface has been shown as a concave surface 112 having the same radius of curvature of the guided surface of the cylindrical drill tube. It will be appreciated that while a circular arc of a guide surface corresponding to a radius of curvature of a cylindrical drill tube is preferred, a plurality of complementary geometries could be used for the guide surface and the guiding surface.

In the present invention, if the surgeon were to place the drill tube 92 such that the axis $X_D$—$X_D$ of the drill tube 92 is not parallel to the longitudinal axis $X_2$—$X_2$ of the centering guide $100_2$, such misalignment could be detected at the proximal end $104_2$ of the guide $100_2$ and be indicated by a spacing between the centering guide $100_2$ and the drill tube 92. An alternative embodiment would be to provide a guiding surface on the centering guide which locks with a guided surface on the drill tube such that nonparallel alignment of the axis of the drill tube and the centering guide is not possible. For example, the guide surface 112' on the centering guide 100' could be dovetail grooved and the guided surface on the drill tube 92' could be a complementary shaped dovetail rail 93' which slides within the dovetail groove 112'. Such a modification would preclude non-parallel alignment of the axis $X_D'$–$X_D'$ of the drill tube 92' and the longitudinal axis X'—X' of the centering guide 100'. However, such a modification would require accurate alignment of the drill tube 92', whereas in the preferred embodiment previously disclosed, the drill tube 92 may be rotated about its axis $X_D$—$X_D$.

L. Multi-Lumen Drill Tube

The ability to maintain accurate alignment between two implants inserted into the intervertebral disc space can be facilitated by early establishment and continued maintenance of parallel operating fields at adjacent implant sites. Once the surgeon has determined the angular orientation of the implants (e.g., relative to the sagittal and/or transverse plane of the vertebral column), a multi-lumen drill tube as described below ensures that the relative positioning of the implants is maintained throughout preparation of the bores that will receive the implants.

FIGS. 57–59 illustrate one embodiment of a multi-lumen drill tube 400. Multi-lumen drill tube 400 includes a distal end 411 and a proximal end 412. The multi-lumen drill tube 400 includes a first elongate lumen 413 surrounded by an elongate wall 414 and a second elongate lumen 415 surrounded by elongate wall 416. Referring to FIG. 59, taken at line 59—59 of FIG. 57, it will be appreciated that in the illustrated embodiment the cross-sectional geometry of each of elongate lumens 413 and 415 can be circular. Between the walls 414 and 416, multi-lumen drill tube 400 includes a guiding arrangement 418, such as channel 419, for receiving an alignment guide.

As used herein, an "alignment guide" provides for alignment of the multi-lumen drill tube 400 at a selected location relative to the intervertebral disc space. Generally, a first portion of the alignment guide is placed in the intervertebral disc space and a second portion extends beyond the margins of opposing vertebrae for alignment of the multi-lumen drill tube 400. The guiding arrangement 418 of the multi-lumen drill tube 400 is configured for complementary fit with the extended portion of the alignment guide.

In some embodiments, an alignment guide can be a centering guide such as $100_1$ illustrated in FIGS. 10–12. Thus, according to this embodiment, distraction portion $106_1$ of centering guide $100_1$ can be inserted into the intervertebral disc space. The remainder of centering guide $100_1$ provides a second portion for complementary fit with the guiding arrangement 418 of multi-lumen drill tube 400.

In an alternative embodiment, an alignment guide can be a centering guide $100_5$ as illustrated in FIG. 60. According to this embodiment, centering guide $100_5$ includes opposing notches 425 in side edges $108_5$, the function of which will be further described below.

Referring to FIGS. 58–60, the cross-sectional diameter of each of lumens 413 and 415 can be the same. As described for drill tube 92, multi-lumen drill tubes 400 having different lumen sizes can be provided for different size spinal implants. In addition, it is foreseen that an individual multi-lumen drill tube having lumens with different diameters could also be advantageous for some procedures. Generally, the lumen diameters are selected to slip in close tolerance to a particular sized implant.

The illustrated multi-lumen drill tube 400 includes a proximal collar 426 at proximal end 412 and a distal collar 427 at distal end 411. The collars maintain walls 414 and 416 in a parallel relationship. The proximal collar 426 has a proximal flange 428 spaced apart from a distal flange 429. One function of a flanged proximal collar 426 is that the outer perimeter dimension of the flange can be constant among multi-lumen drill tubes having different lumen diameters. Thus, instruments that may be used with the multi-lumen drill tube 400, such as the below-described drill depth guide, can be sized to work with different multi-lumen drill tubes regardless of lumen size.

At the distal end 411, multi-lumen drill tube 400 includes an anchoring arrangement 430 for attaching the multi-lumen drill tube 400 to opposing vertebral bodies. In the illustrated embodiment, the anchoring arrangement includes teeth 431. The teeth 431 can have a length $T_L$ of preferably about 3 mm. The valleys 432 between the teeth 431 provide stop surfaces at the bone surface as teeth 431 are forced into the vertebrae.

In addition, the distal end 411 of multi-lumen drill tube 400 can include lateral paddles 433 and 434 on diametrically opposed aspects of walls 414 and 416, respectively. In use, paddles 433 and 434 are inserted into the intervertebral disc space and function to keep blood vessels or other tissues outside the surgical field within the multi-lumen drill tube 400.

The walls surrounding lumens 413 and 415 do not need to be complete. That is, walls 414 and 416 can also each include one or more openings such as elongate slots (not shown) along some or all of the length of wall 414 and 416. The openings provide for easier cleaning of multi-lumen drill tube 400.

The ability to separate the multi-lumen drill tube 400 from the alignment guide permits a single multi-lumen drill tube 400 to be advantageously used with centering guides that provide different amounts of distraction spacing or different degrees of lordosis. In addition, if the multi-lumen drill tube 400 includes teeth 431 for anchoring the tube to the vertebral bodies, the ability of the multi-lumen drill tube 400 to move relative to the alignment guide permits anchoring the multi-lumen guide tube to the vertebral bodies regardless of the depth of penetration of the alignment guide into the disc space.

Figure 61:
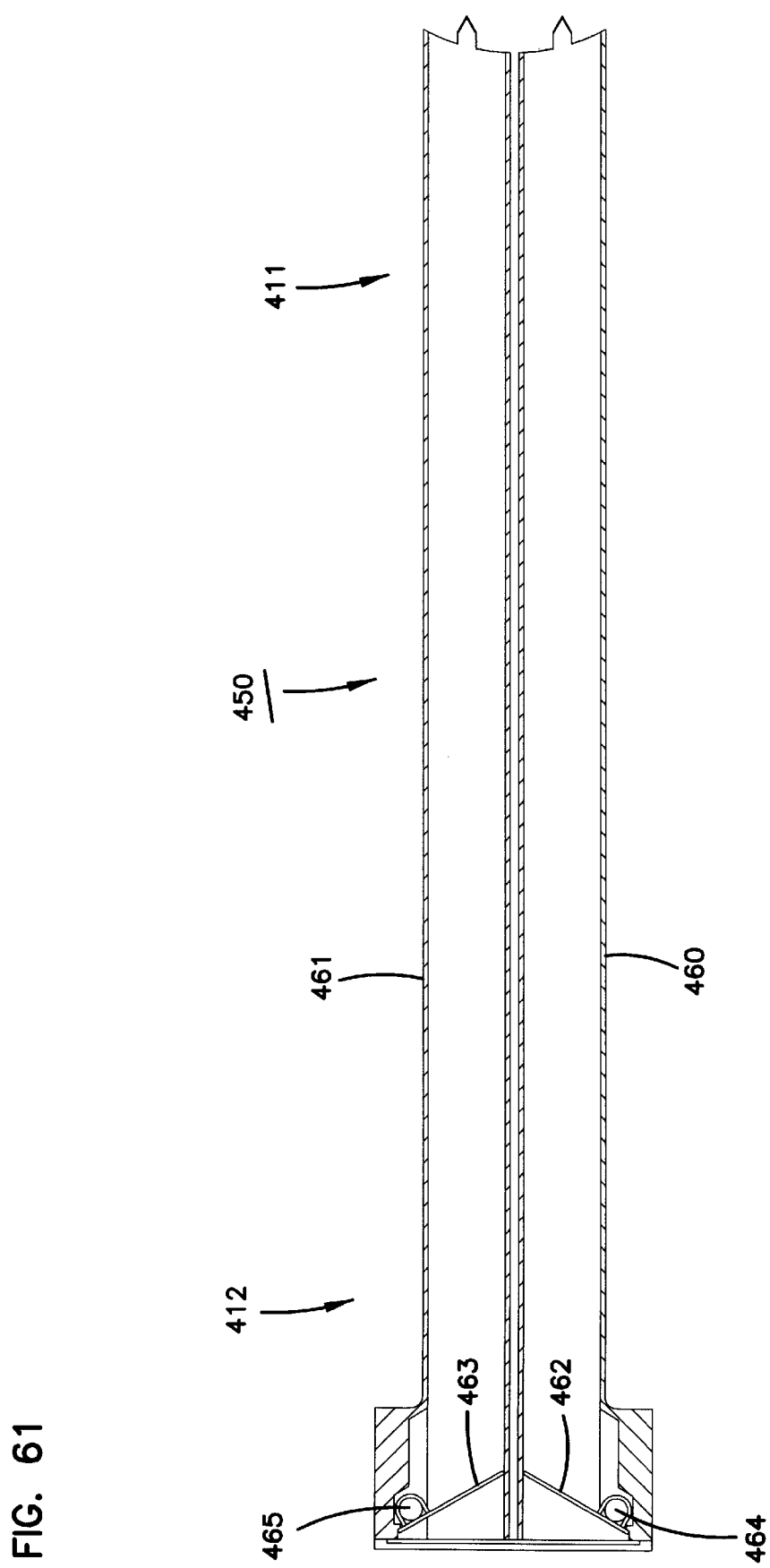
FIG. 61 is a longitudinal cross-section view of an alternative embodiment of a multi-lumen drill tube.

A multi-lumen drill tube can be advantageously used for laparoscopic placement of an implant 10 through an anterior approach. FIG. 61 is a longitudinal cross-section view of another embodiment of a multi-lumen drill tube 450 particularly advantageous for laparoscopic use. In this embodiment, the proximal end 412 of lumens 460 and 461 each include a seal 462 and 463. The seals 462 and 463 can pivot on axes 464 and 465, respectively, to maintain insufflation within the lumens 460 and 461. Thus, to pass an instrument, such as a laparoscopic instrument, into lumen 461, seal 463 is pushed distally around axis 465. Once the instrument is passed into the lumen 461, seal 463 can rotate proximally about axis 465 back to its starting position to form a seal around the instrument. Springs can be used to bias seals 462 and 463 in the proximally closed position.

M. Alignment Guide Insertion Tool

Figure 62:
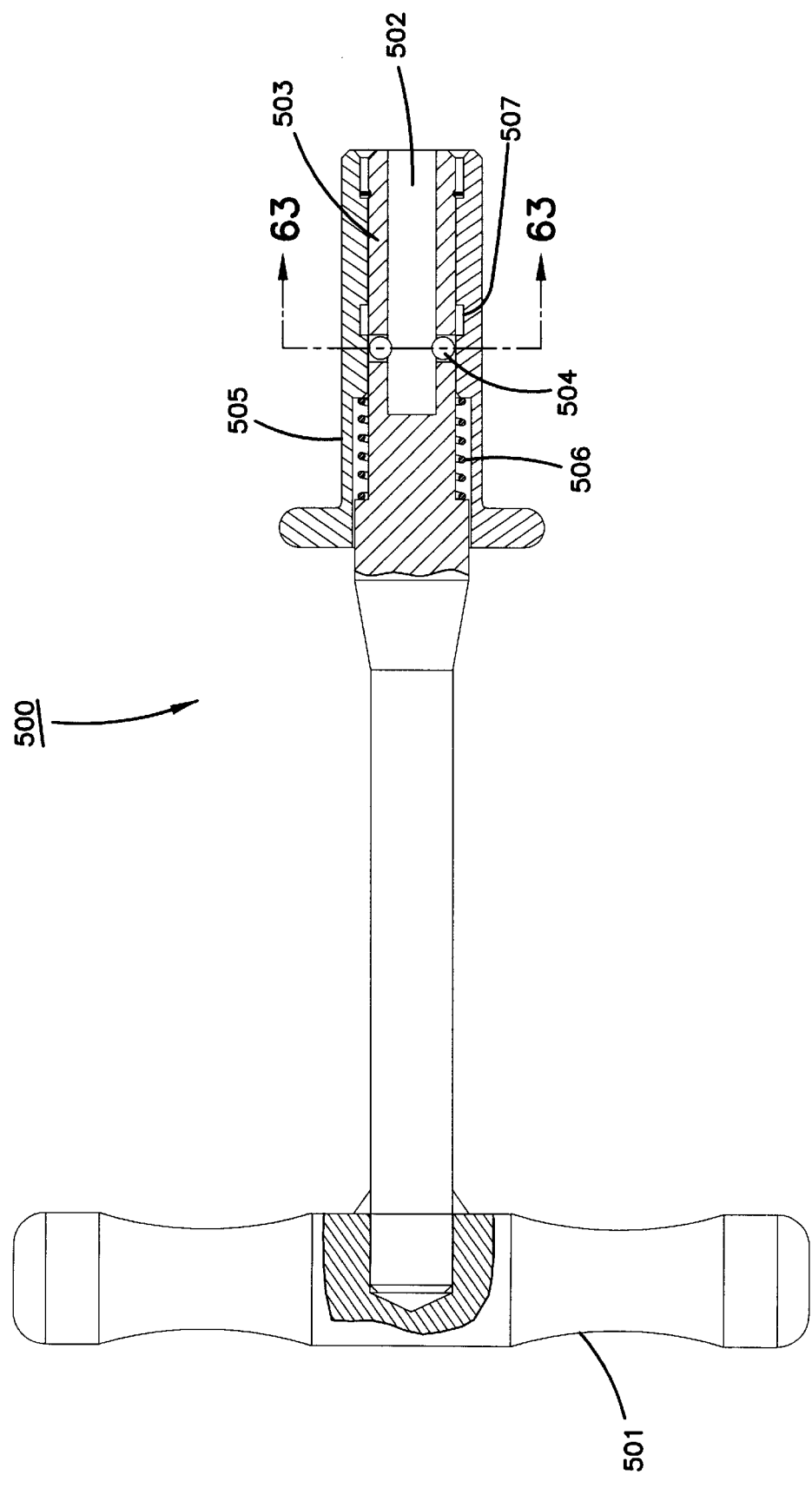
FIG. 62 is a longitudinal cross-section view of an insertion tool for an alignment guide according to the invention.
Figure 64:
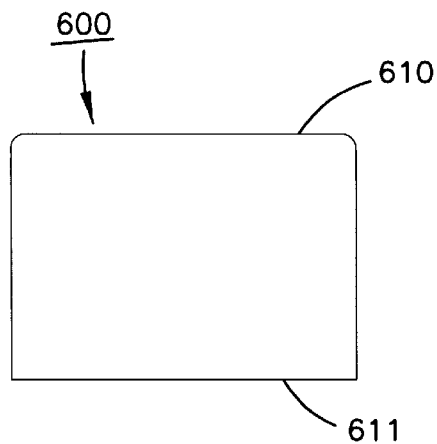
FIG. 64 is a long side view of an embodiment of a drill depth guide of the invention.

FIGS. 62–63 illustrate an insertion tool 500 for assisting insertion of an alignment guide such as centering guide $100_5$ in FIG. 60. Insertion tool 500 permits concussive advancement of the centering guide $100_5$ by tapping on handle 501. In addition, insertion tool 500 provides for rotation or removal of an alignment guide such as centering guide $100_5$.

The insertion tool 500 includes a female receptacle 502 for slidably mounting over a portion of centering guide $100_5$. The receptacle 502 is shaped for complementary fit with the centering guide $100_5$ as can be appreciated in the cross-section view of FIG. 63. A receptacle wall 503 surrounds receptacle 502 and includes one or more retractable detents 504 which can interdigitate with notches 425 of centering guide $100_5$ to hold the centering guide $100_5$ within receptacle 502. Insertion tool 500 includes a sleeve 505 which is biased towards the distal end of the tool 500 by, for example, spring 506. When sleeve 505 is moved proximally, detent 504 can move outwardly into recess 507 permitting withdrawal at the detent 504 from notches 425 of centering guide $100_5$ for removing centering guide $100_5$ from the insertion tool 500.

N. Drill Depth Guide

Figure 65:
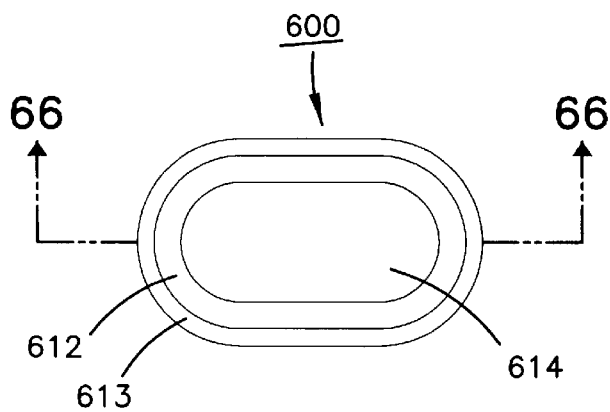
FIG. 65 is an end-on view of the distal end of the drill depth guide of FIG. 64.
Figure 66:
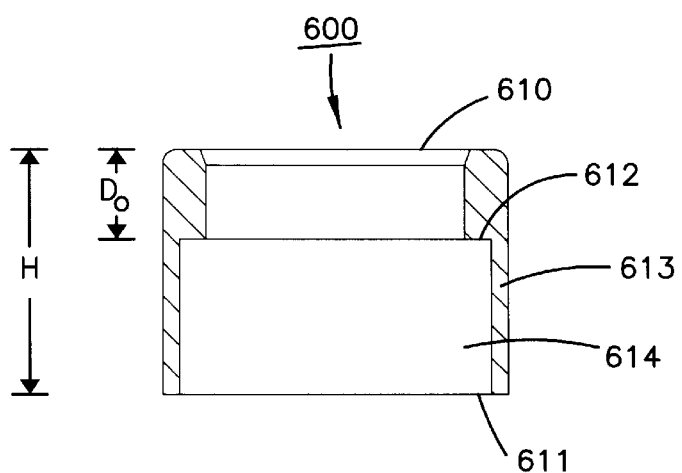
FIG. 66 is a longitudinal cross-section view taken through line 66—66 of the drill depth guide of FIG. 65.
Figure 67:
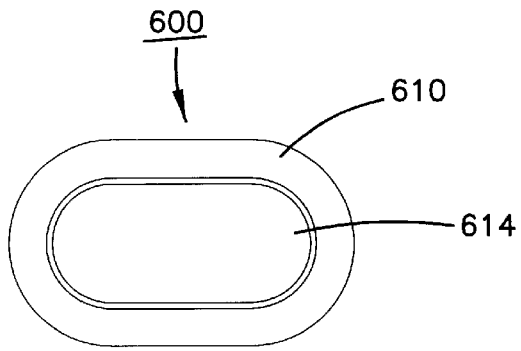
FIG. 67 is an end-on view through the proximal end of the drill depth guide of FIG. 64.

FIGS. 64–67 illustrate an embodiment of a drill depth guide 600 also referred to as a spacer cap. Spacer cap 600 can be removably mounted to the proximal end of a multi-lumen drill tube for selectively controlling the depth of penetration of a tool passed through a lumen of the multi-lumen drill tube. Using multi-lumen drill tube 400 as an example, the illustrated spacer cap 600 is oval shaped for complementary fit over proximal flange 428 at the proximal end of multi-lumen drill tube 400. FIG. 67 is an end-on view of the proximal end 610 of spacer cap 600 and FIG. 65 is an end-on view of the distal end 611 of spacer cap 600. As illustrated in the cross-section view of FIG. 66, taken through line 66-66 of FIG. 65, spacer cap 600 includes a shoulder 612 projecting axially from the wall 613 surrounding lumen 614 of the spacer cap 600. For a given spacer cap height H, the distance $D_0$ between shoulder 612 and the proximal end 610 of spacer cap 600 is equal to the length of spacer cap 600 that extends distally beyond the proximal end of a multi-lumen drill tube 400. In the illustrated embodiment, when in use, shoulder 612 is seated on the proximal flange 428 of proximal collar 426.

Providing multiple spacer caps 600 in a kit, each having a different distance $D_0$, will permit the surgeon to select a spacer cap 600 having the appropriate distance $D_0$ for a selected depth of penetration of an instrument passed through multi-lumen drill tube 400. That is, increasing distance $D_0$ directly decreases the depth of insertion of a bore or other tool into the multi-lumen drill tube because, for example, a flared flange such as 158 on bone tap 142 (FIG. 26) acts as a stop against the proximal end of 610 of the spacer cap 600.

Figure 68:
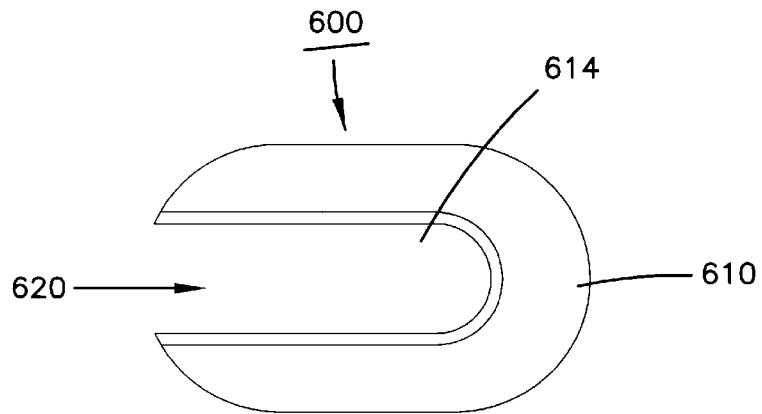
FIG. 68 is an end-on view of the proximal end of a second embodiment of a drill depth guide.
Figure 69:
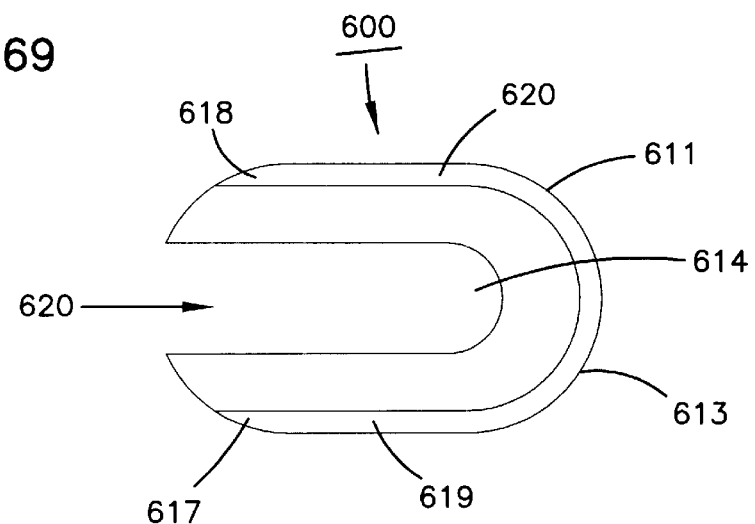
FIG. 69 is an end-on view of the distal end of one embodiment of the drill depth guide of FIG. 68.
Figure 70:
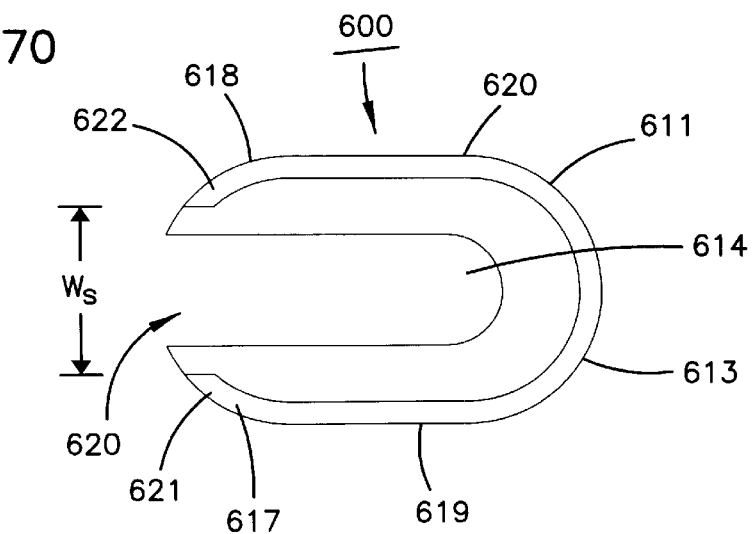
FIG. 70 is an end-on view of the distal end of a second embodiment of the drill depth guide of FIG. 68.

Referring to FIGS. 68–70, in some embodiments, a spacer cap 600 can include a slot 620 in wall 613 extending from the distal end 611 of spacer cap 600 to the proximal end 610. Slot 620 provides for sliding the spacer cap 620 laterally onto the proximal end of the multi-lumen drill tube, rather than over the proximal end.

Referring to the distal end views of FIGS. 69 and 70, two embodiments of a spacer cap 600 with a slot 620 are shown. In the embodiment of FIG. 69, the terminal ends 617 and 618 of opposing side walls 619 and 620, respectively, are parallel. In the embodiment of FIG. 70, the terminal ends 617 and 618 are extended beyond parallel to form detents 621 and 622, respectively. The detents 621 and 622 narrow the width $W_S$ of slot 620 to less than the width $W_T$ of the multi-lumen drill tube 400. (See FIG. 58). Thus, the detents 621 and 622 help retain the spacer cap 600 in position when inserted laterally onto the proximal end 412 of multi-lumen drill tube 400.

After identification of the two vertebral bodies which are to be fused together, the surgeon identifies an implant of desired size and determines the appropriate amount of distraction to be applied between the vertebrae before placement of the implant. The appropriate alignment guide such as centering guide 100 that provides the desired distraction and degree of lordosis is inserted at about the midline of the intervertebral space between opposing vertebrae.

Once the centering guide is secured in the disc space at the desired insertion depth, the guiding arrangement of the multi-lumen drill tube is passed over the centering guide to the anterior surface of the vertebral bodies. If an anchoring arrangement is present, the multi-lumen drill tube is passed until the attachment arrangement is near the anterior margins of the vertebral bodies on either side of the affected disc space. After verifying that all soft tissue structures are free of damage by the anchoring arrangement, the multi-lumen drill tube is tapped into the vertebrae. If paddles (432 and 433 of FIG. 58) are present, they are oriented to pass into the disc space.

Once the multi-lumen drill tube is in place, the insertion bores can be prepared using known methods, In addition, a drill depth guide, such as a spacer cap illustrated in FIGS. 63–68, can be placed on the proximal end of the multi-lumen drill tube to control the depth of insertion of the tools into the multi-lumen drill tube.

From the foregoing detailed description of the present invention it has been shown how the objects of the invention have been obtained in a preferred manner. However, modifications and equivalence of the disclosed concepts such as those which would occur to one of ordinary skill in the art are intended to be included within the scope of the present invention.

What is claimed is:

1. A surgical method for implanting a spinal fusion implant into a disc space separating a first vertebra and a second vertebra, said method comprising:

inserting a distal end of a centering guide into said disc space with said centering guide extending along a longitudinal axis from said distal end to a proximal end exterior of said disc space;

selecting a multi-lumen drill tube comprising first and second elongate lumens having a guiding arrangement therebetween;

passing said multi-lumen drill tube over a portion of said centering guide extending from said disc space such that said centering guide is positioned within said guiding arrangement between said first and second lumens.

2. A method according to claim 1 comprising selecting said distal end to be sized to distract said disc space upon insertion of said distal end into said disc space and distracting said disc space by insertion of said distal end into said disc space.

3. A method according to claim 2 comprising inserting said distal end from an anterior approach and selecting said distal end to have opposite side edges defining an angle approximate to a desired angle of lordosis between said disc space.

4. The method according to claim 1 further comprising:

inserting a drill through a first lumen of said multi-lumen drill tube and boring a first bore;

inserting an implant into said first bore;

inserting a drill through a second lumen of said multi-lumen drill tube and boring a second bore; and inserting an implant into said second bore.

5. A method according to claim 1 wherein said centering guide includes a plurality of x-ray detectable indicia at a plurality of positions at said distal end.

6. A multi-lumen drill tube for implanting a spinal fusion device between opposing vertebral bodies, said multi-lumen drill tube comprising:

a first elongate lumen;

a second elongate lumen; and a guiding arrangement between said first and second elongate lumens configured for receiving an alignment guide positioned between said opposing vertebral bodies.

7. The multi-lumen guide according to claim 6 wherein said guiding arrangement is a channel passing between said first and second elongate lumens.

8. The multi-lumen guide according to claim 7 wherein said channel includes diametrically opposed concave surfaces.

9. The multi-lumen drill tube according to claim 6 having a first end with an anchoring arrangement for securing said multi-lumen drill tube to said vertebral bodies.

10. The multi-lumen drill tube according to claim 9 wherein said anchoring arrangement comprises at least two teeth.

11. The multi-lumen drill tube according to claim 6 wherein said first elongate lumen is defined by a first wall and said second elongate lumen is defined by a second wall, said first wall having a first wall opening and said second wall having a second wall opening.

12. The multi-lumen drill tube according to claim 9 wherein said first end further comprises at least one lateral paddle.

13. The multi-lumen drill tube according to claim 12 wherein said first end comprises two diametrically opposing lateral paddles.

14. A multi-lumen drill tube according to claim 6 wherein said alignment guide is a centering guide.

15. A kit for placement of a spinal implant between opposing vertebral bodies, the kit comprising:
   a centering guide for insertion into a disc space between opposing vertebral bodies; and
   a multi-lumen drill tube comprising:
   (i) a first elongate lumen;
   (ii) a second elongate lumen; and
   (iii) a guiding arrangement between said first and second elongate lumens configured for receiving an aligning guide positioned between said opposing vertebral bodies.

16. A kit according to claim 15 further comprising a spacer cap.

17. A kit according to claim 16 wherein said spacer cap comprises:
   a hollow oval body having
   (i) a first end and a second end;
   (ii) an interior surface and an exterior surface, said interior surface having an axially projecting shoulder;
   (iii) a first longitudinal wall diametrically opposite a second longitudinal wall; and
   (iv) a first curved wall diametrically opposite a second curved wall.

18. A kit according to claim 17 wherein said first curved wall has a slot therethrough.

19. A kit according to claim 18 wherein a width dimension of said slot is less than a width of a proximal end of said multi-lumen drill tube.

20. An insertion tool for attaching to an alignment guide, said insertion tool comprising:
   a proximal end having a handle;
   a distal end, said distal end comprising:
   (a) a female receptacle; and
   (b) a sleeve having a first position and a second position such that when said sleeve is in said first position at least one detent protrudes into said female receptacle and when in said second position said at least one detent does not protrude into said female receptacle.

* * * * *

UNITED STATES PATENT AND TRADEMARK OFFICE
CERTIFICATE OF CORRECTION

PATENT NO. : 6,059,790
DATED : May 9, 2000
INVENTOR(S) : Sand et al.

Page 1 of 1

It is certified that error appears in the above-identified patent and that said Letters Patent is hereby corrected as shown below:

Column 6,
Line 55, "$Y_0$-$Y_0$" should read -- $Y_1$-$Y_1$ --

Column 7,
Line 49, "1002" should read -- $100_2$ --

Column 9,
Line 4, "DR" should read -- $D_R$ --

Column 11,
Line 4, "TD" should read -- $T_D$ --

Column 12,
Line 13, "1002" should read -- $100_2$ --

Signed and Sealed this

Thirteenth Day of November, 2001

Attest:

*Nicholas P. Godici*

NICHOLAS P. GODICI
*Attesting Officer*     *Acting Director of the United States Patent and Trademark Office*